(12) United States Patent
Bamberg et al.

(10) Patent No.: US 8,748,578 B2
(45) Date of Patent: Jun. 10, 2014

(54) MUTANT CHANNELRHODOPSIN 2

(75) Inventors: Ernst Bamberg, Kelkheim (DE);
Christian Bamann, Frankfurt (DE);
Sonja Kleinlogel, Bern (CH); Phillip Wood, Schmelz (DE); Robert E. Dempski, Holden, MA (US)

(73) Assignee: Max-Planck-Gesellschaft zur Foerderrung der Wissenschaften e.V., Munich (DE)

( * ) Notice: Subject to any disclaimer, the term of this patent is extended or adjusted under 35 U.S.C. 154(b) by 0 days.

(21) Appl. No.: 13/821,353

(22) PCT Filed: Sep. 8, 2011

(86) PCT No.: PCT/EP2011/065510
§ 371 (c)(1),
(2), (4) Date: May 21, 2013

(87) PCT Pub. No.: WO2012/032103
PCT Pub. Date: Mar. 15, 2012

(65) Prior Publication Data
US 2013/0281379 A1    Oct. 24, 2013

Related U.S. Application Data

(60) Provisional application No. 61/380,793, filed on Sep. 8, 2010.

(30) Foreign Application Priority Data

Sep. 8, 2010  (EP) .................................... 10175832

(51) Int. Cl.
*C07K 14/215* (2006.01)
*C07K 14/405* (2006.01)
*G01N 33/68* (2006.01)

(52) U.S. Cl.
USPC ........ 530/350; 514/17.4; 514/17.7; 514/18.1; 514/19.3; 435/235.1; 435/325; 435/358; 435/369; 435/365; 435/353; 435/375

(58) Field of Classification Search
None
See application file for complete search history.

(56) References Cited

U.S. PATENT DOCUMENTS

2005/0202398 A1   9/2005   Hegemann et al.
2011/0086421 A1   4/2011   Hegemann et al.

FOREIGN PATENT DOCUMENTS

EP      2 112 501 A1       10/2009
WO      WO 03/084994 A2    10/2003

OTHER PUBLICATIONS

Lin et al., A user's guide to channelrhodopsin variants: features, limitations and future developments. Exp Physiol 96.1 pp. 19-25 (2011) first published online Jul. 9, 2010.*
Sugiyama et al., Photocurrent attenuation by a single polar-to-nonpolar point mutation of channelrhodopsin-2. Photochem. Photobiol. Sci., 2009, 8, 328-336 First published on the web Jan. 22, 2009.*
International Search Report Issued Nov. 8, 2011 in PCT/EP2011/065510.

(Continued)

*Primary Examiner* — Jeffrey Stucker
*Assistant Examiner* — Aurora M Fontainhas
(74) *Attorney, Agent, or Firm* — Oblon, Spivak, McClelland, Maier & Neustadt, L.L.P.

(57) ABSTRACT

The invention relates to mutant channelrhodopsins having improved properties, nucleic acid constructs encoding same, expression vectors carrying the nucleic acid construct, cells comprising said nucleic acid construct or expression vector, and their respective uses.

11 Claims, 9 Drawing Sheets

(56) References Cited

OTHER PUBLICATIONS

Georg Nagel et al., "Channelrhodopsin-2, a directly light-gated cation-selective membrane channel", PNAS, vol. 100, No. 24, Nov. 25, 2003, pp. 13940-13945.

Georg Nagel et al., "Light Activation of Channelrhodopsin-2 in Excitable Cells of *Caenorhabditis elegans* Triggers Rapid Behavioral Responses", Current Biology, vol. 15, Dec. 20, 2005, pp. 2279-2284.

Edward S. Boyden et al., "Millisecond-timescale, genetically targeted optical control of neural activity", Nature Neuroscience, vol. 8, No. 9, Sep. 2005, pp. 1263-1268.

Feng Zhang et al., "Multimodal fast optical interrogation of neural circuitry", Nature, vol. 446, Apr. 5, 2007, 9 pages.

Christian Bamann et al., "Structural Guidance of the Photocycle of Channelrhodopsin-2 by an Interhelical Hydrogen Bond", Biochemistry, vol. 49, No. 2, pp. 267-278, 2010.

André Berndt et al., "Bi-stable neural state switches", Nature Neuroscience, vol. 12, No. 2, Feb. 2009, pp. 229-234.

John Y. Lin et al., "Characterization of Engineered Channelrhodopsin Variants with Improved Properties and Kinetics", Biophysical Journal, vol. 96, No. 5, Mar. 2009, pp. 1803-1814.

Pamela S. Lagali et al., "Light-activated channels targeted to ON bipolar cells restore visual function in retinal degeneration", Nature Neuroscience, vol. 11, No. 6, Jun. 2008, pp. 667-675.

Anding Bi et al., "Ectopic Expression of a Microbial-Type Rhodopsin Restores Visual Responses in Mice with Photoreceptor Degeneration", Neuron, vol. 50, Apr. 6, 2006, pp. 23-33.

B. Frankenhaeuser et al., "The Action of Calcium on the Electrical Properties of Squid Axons", J. Physiol., vol. 137, 1957, pp. 218-244.

Beetil Hille, "Modification of Gating in Voltage-Sensitive Channels", Jou. Channels of Excitable Membranes, 3$^{rd}$ Edition, 2001, pp. 635-662.

Lisa A. Gunaydin et al., "Ultrafast optogenetic control", Nature Neuroscience, vol. 13, No. 3, Mar. 2010, 7 pages.

Christian Bamann et al., "Spectral Characteristics of the Photocycle of Channelrhodopsin-2 and Its Implication for Channel Function", J. Mol. Biol., vol. 375, 2008, pp. 686-694.

Katrin Feldbauer et al., "Channelrhodopsin-2 is a leaky proton pump", PNAS, vol. 106, No. 30, Jul. 28, 2009, pp. 12317-12322.

John H. Caldwell et al., "Increases in Intracellular Calcium Triggered by Channelrhodopsin-2 Potentiate the Response of Metabotropic Glutamate Receptor mGluR7", The Journal of Biological Chemistry, vol. 283, No. 36, Sep. 5, 2008, 10 pages.

Wolf-Michael Weber, "Ion currents of *Xenopus laevis* oocytes: state of the art", Biochimica et Biophysica Acta, vol. 1421, 1999, pp. 213-233.

Senthil Thyagarajan et al., "Visual Function in Mice with Photoreceptor Degeneration and Transgenic Expression of the Channelrhodopsin 2 in Ganglion Cells", The Journal of Neuroscience, vol. 30, No. 26, Jun. 30, 2010, pp. 8745-8758.

B. Hiiie et al., "Negative surface charge near sodium channels of nerve: divalent ions, monovalent ions, and pH", Phil. Trans. R. Soc. Lond., Series B, vol. 270, No. 908, pp. 301-318 with cover page, 1975.

Robert U. Muller et al., "The Effect of Surface Charge on the Voltage-Dependent Conductance Induced in Thin Lipid Membranes by Monazomycin", The Journal of General Physiology, vol. 60, Sep. 1, 1972, pp. 285-306.

E.S. Louise Faber et al., "Calcium-Activated Potassium Channels: Multiple Contributions to Neuronal Function", The Neuroscientist, vol. 9, No. 3, 2003, pp. 181-194 with cover page.

Nathan H. Joh et al., "Similar Energetic Contributions of Packing in the Core of Membrane and Water-Soluble Proteins", J. Am. Chem. Soc., vol. 131, No. 31, 2009, pp. 10846-10847.

Sriram Subramaniam et al., "Electron diffraction studies of light-induced conformational changes in the Leu-93 → Ala bacteriorhodopsin mutant", Proc. Natl. Acad. Sci. USA, vol. 94, Mar. 1997, pp. 1767-1772.

Siriram Subramaniam et al., "Replacement of leucine-93 by alanine or threonine slows down the decay of the N and O intermediates in the photocycle of bacteriorhodopsin: Implications for proton uptake and 13-*cis*-retinal → all-*trans*-retinal reisomerization", Proc. Natl. Acad. Sci. USA, vol. 88, Aug. 1991, pp. 6873-6877.

Melanie Nack et al., "The DC gate in Channelrhodopsin-2: crucial hydrogen bonding interaction between C128 and D156", Photochem. Photobiol. Sci., vol. 9, 2010, pp. 194-198 with cover page.

Volker Busskamp et al., "Genetic Reactivation of Cone Photoreceptors Restores Visual Responses in Retinitis Pigmentosa", Science, vol. 329, Jul. 23, 2010, pp. 413-417 with cover page.

Graham C. R. Ellis-Davies, "Neurobiology with Caged Calcium", Chem. Rev., vol. 108, No. 5, 2008, pp. 1603-1613.

Claudius Lorenz et al., "Heteromultimeric CLC chloride channels with novel properties", Proc. Natl. Acad. Sci. USA, vol. 93, Nov. 1996, pp. 13362-13366.

Mariacarmela Allocca et al., "Novel Adeno-Associated Virus Serotypes Efficiently Transduce Murine Photoreceptors", Journal of Virology, vol. 81, No. 20, Oct. 2007, pp. 11372-11380.

Pablo de Felipe et al., "*E unum plubrius*: multiple proteins from a self-processing polyprotein", TRENDS in Biotechnology, vol. 24, No. 2, Feb. 2006, pp. 68-75.

William Humphrey et al., "VMD: Visual Molecular Dynamics", Journal of Molecular Graphics, vol. 14, 1996, pp. 33-38.

André Berndt et al., "Two Open States with Progressive Proton Selectivities in the Branched Channelrhodopsin-2 Photocycle", Biophysical Journal, vol. 98, No. 5, Mar. 2010, pp. 753-761.

Sonja Kleinlogel et al., "Ultra light-sensitive and fast neuronal activation with the $Ca^{2+}$-permeable channelrhodopsin CatCh", Nature Neuroscience, vol. 14, No. 4, Apr. 2011, 8 pages.

Maria Müller et al., "Projection Structure of Channelrhodopsin-2 at 6 A Resolution by Electron Crystallography", Journal of Molecular Biology, vol. 414, 2011, pp. 86-95.

\* cited by examiner

MUTANT CHANNELRHODOPSIN 2

The invention relates to mutant channelrhodopsins having improved properties, nucleic acid constructs encoding same, expression vectors carrying the nucleic acid construct, cells comprising said nucleic acid construct or expression vector, and their respective uses.

BACKGROUND OF THE INVENTION

The light-gated, inwardly rectifying cation channel, channelrhodopsin-2 (ChR2) has become a preferred tool for the targeted light-activation of neurons both in vitro and vivo[1-4]. Although wild-type (WT) ChR2 can be employed for light-induced depolarization, there is an ongoing search for ChR2 mutants with increased light-sensitivity for potential future clinical applications (WO 03/084994 and [5-7]). Higher efficacy would enable depolarization of cell layers distant from the applied light source despite the low optical transmittance of, e.g., brain tissue. An increase in light sensitivity would also solve the problem of potential cell damage under continuous illumination due to the high blue light intensities required for full WT ChR2 activation ($10^{18}$-$10^{19}$ ph s$^{-1}$ cm$^{-2}$ at 480 nm). Variants with higher light sensitivity are also crucial for research pertaining to the recovery of vision[8,9]. On the protein level, higher light efficacy can only be achieved by increasing the life-time of the open state and/or by elevating the unit conductance of the channel, as the light sensitivity per se can be improved only marginally due to the nature of the ChR2 chromophore retinal. Previous research has demonstrated that mutations at positions C128 and D156 in helix 3 and 4, respectively, resulted in markedly slowed channel kinetics with open life-times up to 30 minutes and more, yielding a 500-fold or even higher light-sensitivity[5,6]. These C128 and D156 mutants can be switched off at variable open times by red light. Despite the superior light-sensitivity, their slow closing kinetics remains a limiting factor for their applicability.

Accordingly, there is still a need for light-inducible cation channels exhibiting a higher light sensitivity and faster response kinetics.

SUMMARY OF THE INVENTION

Since it is known that a cell's inner membrane surface potential is strongly influenced by $Ca^{++}$, modifying submembraneous intracellular $Ca^{++}$ levels will lead to depolarization of the membrane and in neurons to activation of voltage-gated $Na^+$ channels. Thus, the inventors hypothesized that the light-sensitivity of a neuron can be indirectly increased by elevating its inner membrane surface potential via $Ca^{++}$-influx. The inventors surprisingly found a ChR2 mutant with an enhanced $Ca^{++}$-permeability, in the following designated as CatCh, i.e. Calcium translocating Channelrhodopsin. CatCh has a four-fold higher $Ca^{++}$-permeability, a 70-fold higher light-sensitivity and faster response kinetics when expressed in hippocampal neurons compared to the WT ChR2. The enhanced light sensitivity and fast kinetics are shown to stem from the relatively high light-gated $Ca^{++}$-influx, which elevates the inner membrane surface potential and activates $Ca^{++}$-activated large conductance potassium (BK) channels. An increase in $[Ca^{++}]_i$ elevates the internal surface potential, facilitating activation of voltage-gated $Na^+$-channels and indirectly increasing light-sensitivity. Repolarization following light-stimulation is markedly accelerated by $Ca^{++}$-dependent BK-channel activation. CatCh exemplifies a new principle by which light-gated channels can be engineered to increase the light sensitivity of neuronal stimulation. Its characteristics such as triggering precise and fast action potentials while requiring low light intensities for activation open the way for the use of light-gated channels in clinical applications.

Accordingly, in a first aspect, the invention relates to a light-inducible ion channel, wherein the light-inducible ion channel comprises an amino acid sequence which has at least 70% homology to the amino acid sequence shown in positions 1-309 of SEQ ID NO: 1 (CHOP-2), and which comprises a mutation at a position corresponding to L132 in SEQ ID NO: 1.

In a similar second aspect, the invention also relates to a channelrhodopsin, comprising the light-inducible ion channel according to the first aspect and a retinal or retinal derivative. Further, in a third aspect, the invention provides a nucleic acid construct, comprising a nucleotide sequence coding for the light-inducible ion channel according to the first aspect. In still another aspect, the invention provides an expression vector, comprising a nucleotide sequence coding for the light-inducible ion channel according to the first aspect or the nucleic acid construct according to the third aspect.

Moreover, a cell is provided, comprising the channelrhodopsin according to the second aspect, the nucleic acid construct according to the third aspect, or the expression vector according to the fourth aspect.

In addition, the invention pertains to the use of the light inducible ion channel according to the first aspect, the channelrhodopsin of the second aspect, the nucleic acid construct or the expression vector according to the invention, and the cell according to the invention as a medicament. In particular, a use of the expression vector according to the invention in gene therapy is contemplated.

More specifically, the use of the light-inducible ion channel, channelrhodopsin, nucleic acid construct, expression vector, or cell according to the invention in the treatment of blindness or reduced sight is contemplated.

In still another aspect, the invention provides the use of the light-inducible ion-channel according to the first aspect, additionally having threonine, serine, or alanine at a position corresponding to position 128 of SEQ ID NO: 1; and/or alanine at a position corresponding to position 156 of SEQ ID NO: 1, in the ablation of cancer cells.

In a final aspect, the invention relates to the use of a light-inducible ion channel according to the first aspect, or a channelrhodopsin according to the second aspect, or a cell according to the invention in a high-throughput screening.

DETAILED DESCRIPTION OF THE PREFERRED EMBODIMENTS

In a first aspect, the invention relates to a light-inducible ion channel, wherein the light-inducible ion channel comprises an amino acid sequence which has at least 70% identity to the amino acid sequence shown in positions 1-309 of SEQ ID NO: 1 (CHOP-2), more preferably to the amino acid sequence shown in positions 1-315 of SEQ ID NO: 1, or even to the amino acid sequence shown in positions 1-737 of SEQ ID NO: 1, and which comprises a mutation at a position corresponding to L132 in SEQ ID NO: 1.

Wild-type CHOP2 has the following amino acid sequence:

(SEQ ID NO: 1)
```
MDYGGALSAV GRELLFVTNP VVVNGSVLVP EDQCYCAGWI

ESRGTNGAQT ASNVLQWLAA GFSILLLMFY AYQTWKSTCG

WEEIYVCAIE MVKVILEFFF EFKNPSMLYL ATGHRVQWLR

YAEWLLTCPV ILIHLSNLTG LSNDYSRRTM GLLVSDIGTI

VWGATSAMAT GYVKVIFFCL GLCYGANTFF HAAKAYIEGY

HTVPKGRCRQ VVTGMAWLFF VSWGMFPILF ILGPEGFGVL

SVYGSTVGHT IIDLMSKNCW GLLGHYLRVL IHEHILIHGD

IRKTTKLNIG GTEIEVETLV EDEAEAGAVN KGTGKYASRE

SFLVMRDKMK EKGIDVRASL DNSKEVEQEQ AARAAMMMMN

GNGMGMGMGM NGMNGMGGMN GMAGGAKPGL ELTPQLQPGR

VILAVPDISM VDFFREQFAQ LSVTYELVPA LGADNTLALV

TQAQNLGGVD FVLIHPEFLR DRSSTSILSR LRGAGQRVAA

FGWAQLGPMR DLIESANLDG WLEGPSFGQG ILPAHIVALV

AKMQQMRKMQ QMQQIGMMTG GMNGMGGGMG GGMNGMGGGN

GMNNMGNGMG GGMGNGMGGN GMNGMGGGNG MNNMGGNGMA

GNGMGGGMGG NGMGGSMNGM SSGVVANVTP SAAGGMGGMM

NGGMAAPQSP GMNGGRLGTN PLFNAAPSPL SSQLGAEAGM

GSMGGMGGMS GMGGMGGMGG MGGAGAATTQ AAGGNAEAEM

LQNLMNEINR LKRELGE
```

The light inducible ion channel of the invention is a membrane protein with at least 5 transmembrane helices, which is capable of binding a light-sensitive polyene. Transmembrane proteins with 6 or 7 transmembrane helices are preferable. Transmembrane proteins with more than 7 helices, for example 8, 9 or 10 transmembrane helices, are however also covered by the invention. Furthermore, the invention covers transmembrane proteins which in addition to the transmembrane part include C- and/or N-terminal sequences, where the C-terminal sequences can extend into the inside of the lumen enclosed by the membrane, for example the cytoplasm of a cell or the inside of a liposome, or can also be arranged on the membrane outer surface. The same applies for the optionally present N-terminal sequences, which can likewise be arranged both within the lumen and also on the outer surface of the membrane. The length of the C- and/or N-terminal sequences is in principle subject to no restriction; however, light-inducible ion channels with C-terminal sequences not embedded in the membrane, with 1 to 1000 amino acids, preferably 1 to 500, especially preferably 5 to 50 amino acids, are preferred. Independently of the length of the C-terminal sequences, the N-terminal located sequences not embedded in the membrane preferably comprise 1 to 500 amino acids, especially preferably 5 to 50 amino acids. The concept of the transmembrane helix is well known to the skilled person. These are generally α-helical protein structures, which as a rule comprise 20 to 25 amino acids. However, depending on the nature of the membrane, which can be a natural membrane, for example a cell or plasma membrane, or also a synthetic membrane, the transmembrane segments can also be shorter or longer. For example, transmembrane segments in artificial membranes can comprise up to 30 amino acids, but on the other hand also only a few amino acids, for example 12 to 16.

In a preferred embodiment, the light-inducible ion channel comprises an amino acid sequence which has at least 70% identity, preferably at least 75% identity, more preferably at least 80% identity, even more preferably at least 85% identity, such as at least 90% identity, and most preferably at least 95% identity to the amino acid sequence shown in positions 1-309 of SEQ ID NO: 1.

In another preferred embodiment, the light-inducible ion channel comprises an amino acid sequence which has at least 70% identity, preferably at least 75% identity, more preferably at least 80% identity, even more preferably at least 85% identity, such as at least 90% identity, and most preferably at least 95% identity to the amino acid sequence shown in positions 1-315 of SEQ ID NO: 1.

Generally, an amino acid sequence has "at least x % identity" with another amino acid sequence or SEQ ID NO: 1 above, when the sequence identity between those to aligned sequences is at least x %. Such an alignment can be performed using for example publicly available computer homology programs such as the "BLAST" program provided at the NCBI homepage at http://www.ncbi.nlm.nih.gov/blast/blast.cgi, using the default settings provided therein. Further methods of calculating sequence identity percentages of sets of nucleic acid sequences are known in the art.

Examples for such light-inducible ion channels comprising an amino acid sequence which has at least 70% identity to the amino acid sequence shown in positions 1-309 or 1-315 of SEQ ID NO: 1 is CHOP1 from *C. reinhardtii* (gi:15811379), CHOP2 (gi:167650748) and CHOP1 (gi:167650744) from *Volvox carteri*, or any other ortholog or allelic variant of CHOP2 or CHOP1.

In an even more preferred embodiment, the light-inducible ion channel comprises, preferably consists of the amino acid sequence shown in positions 1-309 of SEQ ID NO: 1 (CHOP-2), except for a mutation at position L132.

In another even more preferred embodiment, the light-inducible ion channel comprises, preferably consists of the amino acid sequence shown in positions 1-315 of SEQ ID NO: 1 (CHOP-2), except for a mutation at position L132.

The mutation at position L132, or at the position corresponding to L132 in SEQ ID NO: 1 may be a substitution, addition and/or a deletion. However, preferably, the mutation is a substitution, more preferably selected from L132C, L132S, L132E, L132D, and L132T, most preferably wherein the substitution is L132C. Even though the experimental data is limited to L132C, it is contemplated that the substitutions L132S, L132E, L132D, and L132T will exhibit similar properties, since all these substitutions will increase the polarity of the channel.

In addition, the light-inducible ion channel comprises further (semi-)conservative substitutions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. Typical semi-conservative and conservative substitutions are:

| Amino acid | Conservative substitution | Semi-conservative substitution |
|---|---|---|
| A | G; S; T | N; V; C |
| C | A; V; L | M; I; F; G |
| D | E; N; Q | A; S; T; K; R; H |

-continued

| Amino acid | Conservative substitution | Semi-conservative substitution |
|---|---|---|
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Furthermore, the skilled person will appreciate that glycines at sterically demanding positions should not be substituted and that proline should not be introduced into parts of the protein which have an alpha-helical or a beta-sheet structure.

In another preferred embodiment, the light-inducible ion channel comprises the consensus motif L(I)DxxxKxxW(F, Y). Amino acids given in brackets can in each case replace the preceding amino acid. This consensus sequence is the motif surrounding the retinal-binding amino acid lysine.

The possibility to activate CatCh with naturally occurring light intensities whilst maintaining high temporal precision makes it a unique candidate particularly for gene-therapeutic visual restoration efforts but also other biomedical applications. Due to its reduced light-requirements, CatCh spikes can be generated even by excitation far from its spectral maximum of 474 nm, e.g. with green light (532 nm—see FIG. 4d). Working at the outer flanks of the action spectrum is feasible due to its reduced light-requirements and facilitates tissue penetration.

Thus, the light-sensitivity of the mutant light-inducible ion channel of the invention is preferably increased by more than 5 times, preferably by more than 10 times, more preferably by more than 20 times, such as 30 times, even more preferably by more than 40 times, such as 50 times, and most preferably by more than 60 times, or even by more than 70 times, as compared to WT CHOP-2 in hippocampal neurons. Further, the mutant light-inducible ion channel of the invention exhibits a stimulation frequency which is increased at least 1.5-fold, more preferably 2-fold, or even more preferably 2.5 fold, compared to WT CHOP-2 as determined by whole-cell electrophysiological recordings in hippocampal neurons. As shown in the examples, WT-Chop2 exhibits a stimulation frequency in hippocampal neurons of about 10 Hz up to about 20 Hz, wherein at 20 Hz signalling is already inaccurate. Further, the skilled person will acknowledge that the intrinsic spike frequency is also dependent on the cell type. For example, auditory cells have an intrinsic spike frequency of up to 500 Hz. Moreover, the experiments have been conducted in vitro, i.e. at ambient temperature. However, the skilled person will expect that the stimulation frequency will be even higher in warm-blooded animals, such as mammals, since the kinetics are also temperature-dependent. Therefore, depending on the cell type and the temperature, it is to be expected that the mutant light-inducible ion channel of the invention may also exhibit a stimulation frequency which is increased at least 5-fold, preferably at least 10-fold, such as at least 20-fold, or at least 30-fold, or more preferably at least 40-fold, at least 50-fold, such as at least 60-fold, or at least 70-fold, even more preferably at least 80-fold, at least 90-fold, or at least 100-fold, most preferably at least 125-fold, such as at least 150-fold, or at least 175-fold, and even most preferably at least 200-fold, compared to WT CHOP-2 as determined by whole-cell electrophysiological recordings. Hippocampal neuron culture and electrophysiological recordings from hippocampal neurons is exemplified in the examples below.

Briefly, Hippocampi are isolated from postnatal P1 Sprague-Dawley rats (Jackson Laboratory) and treated with papain (20 U ml-1) for 20 min at 37° C. The hippocampi are washed with DMEM (Invitrogen/Gibco, high glucose) supplemented with 10% fetal bovine serum and triturated in a small volume of this solution. ~75,000 cells are plated on poly-D-lysine/laminin coated glass cover slips in 24-well plates. After 3 hours the plating medium is replaced by culture medium (Neurobasal A containing 2% B-27 supplement, 2 mM Glutamax-1 and 100 U/ml penicillin and 100 μg/ml streptomycin). Mutant ChR2(L132C)-YFP and ChR2 (WT)-YFP are transfected 5-10 days after plating using the lipofectamine 2000 reagent (Invitrogen). Alternatively, 2-5×109 GC/ml of virus (AAV2/7-CAG-ChR2(L132C)-2A-EGFP-WPRE-bGH) may be added to each well 4-9 days after plating. Representative construction of the Adeno-associated viral vector construct is described in detail in the examples below. Expression becomes visible 5 days post-transduction. No all-trans retinal is added to the culture medium or recording medium for any of the experiments.

For whole-cell recordings in cultured hippocampal neurons, patch pipettes with resistances of 5-10 MΩ are filled with 129 mM potassium gluconate, 10 mM HEPES, 10 mM KCl, 4 mM MgATP and 0.3 mM Na$_3$GTP, titrated to pH 7.2. Tyrode's solution is employed as the extracellular solution (125 mM NaCl, 2 mM KCl, 2 mM CaCl$_2$, 1 mM MgCl$_2$, 30 mM glucose and 25 mM HEPES, titrated to pH 7.4). The nominally Ca$^{++}$-free extracellular solution contains this same solution except that it has 0 mM Ca$^{++}$ and 3 mM Mg$^{++}$. Recordings are conducted in the presence of the excitatory synaptic transmission blockers, 1,2,3,4-tetrahydro-6-nitro-2,3-dioxo-benzo[f]quinoxaline-7-sulfonamide (NBQX, 10 μM, Sigma) and D(−)-2-Amino-5-phosphonopentanoic acid (AP-5, 50 μM, Sigma). For voltage-clamp recordings 1 μM tetrodotoxin is added to the extracellular solution. To inhibit BK-channel activity, 1 mM TEA is added. Recordings are conducted on an inverted Zeiss Axiovert 25 microscope equipped with a fluorescence lamp. Successful protein expression is proven by EGFP- or YFP-mediated fluorescence. Neuronal access resistance is 15-40 MΩ and is monitored for stability throughout the experiment. Electrophysiological signals are amplified using an Axopatch 200A amplifier (Axon Instruments, Union City, Calif.), filtered at 10 kHz, digitized with an Axon Digidata 1600 (50 Hz) and acquired and analyzed using pClamp9 software (Axon Instruments). Photocurrents are evoked using light pulses of various lengths from diode-pumped solid-state lasers (Pusch Opto Tech GmbH; λ1=473 nm, P1=100 mW, λ2=532 nm, P2=50 mW) or 10 ns flashes from an excimer pumped dye laser (Coumarin 2, λ=450 nm). Specific light intensities are intensities at the end of a 400 μm diameter quartz optic fiber (STE-F100/400-Y-VIS/NIR; Laser 2000, Wessling, Germany) at a distance of ~500 μm from the cell. Currents measured from neurons expressing ChR2(L132C)-YFP and ChR2(L132C)-2A-EGFP are identical.

In addition, in another preferred embodiment, the calcium conductivity of the mutant light-inducible ion channel of the invention is increased at least two-fold, preferably at least three-fold, more preferably at least four-fold compared to WT CHOP-2, as determined by Fura-2-imaging on HEK293 cells. In order to determine the calcium conductivity, Fura-2 AM (5 mM; Invitrogen) is loaded at room temperature for 30 min to 1 hour. After loading, the cells are recovered in a 140 mM NaCl solution without $Ca^{++}$ (140 mM NaCl, 7 mM EGTA, 2 mM $MgCl_2$ and 10 mM HEPES). Yellow fluorescent protein is excited by a 500 ms exposure to light using a 460/40 nm filter (Visitron Systems, Puchheim, Germany) to estimate each cell's expression level from its YFP-fluorescence. The solution is then replaced by an extracellular $Ca^{++}$-solution that consists of 90 mM $CaCl_2$, 7 mM EGTA, 2 mM $MgCl_2$ and 10 mM HEPES. After 15 min in the dark the light-gated channels are stimulated for 10 s with blue light (460/40 nm). Fura-2 is excited with 340 nm (340/20) and 380 nm (380/20) and the emitted light (540/80 nm) detected with a CCD camera (all filters from Visitron Systems, Puchheim, Germany).

As implicated above, the mutant light-inducible ion channel may additionally comprise further mutations, preferably substitutions. In one preferred embodiment, the light-inducible ion channel may additionally comprise at least one of the following amino acid residues: aspartic acid at a position corresponding to position 253 of SEQ ID NO: 1; lysine at a position corresponding to position 257 of SEQ ID NO: 1; tryptophan at a position corresponding to position 260 of SEQ ID NO: 1; glutamic acid at a position corresponding to position 123 of SEQ ID NO: 1; histidine or arginine, preferably arginine, at a position corresponding to position 134 of SEQ ID NO: 1; threonine, serine, or alanine at a position corresponding to position 128 of SEQ ID NO: 1; and/or alanine at a position corresponding to position 156 of SEQ ID NO: 1. Accordingly, the mutant light-inducible ion channel may comprise one of the following combinations of amino acid residues at the indicated positions, which positions correspond to SEQ ID NO: 1:

Cys 132+Asp 253; Cys 132+Lys 257; Cys 132+Trp 260; Cys 132+Glu 123; Cys 132+His 134; Cys 132+Arg 134; Cys 132+Thr 128; Cys 132+Ser 128; Cys 132+Ala 128; Cys 132+Ala 156;

Cys 132+Asp 253+Lys 257; Cys 132+Asp 253+Trp 260; Cys 132+Asp 253+Glu 123; Cys 132+Asp 253+His 134; Cys 132+Asp 253+Arg 134; Cys 132+Asp 253+Thr 128; Cys 132+Asp 253+Ser 128; Cys 132+Asp 253+Ala 128; Cys 132+Asp 253+Ala 156;

Cys 132+Lys 257+Trp 260; Cys 132+Lys 257+Glu 123; Cys 132+Lys 257+His 134; Cys 132+Lys 257+Arg 134; Cys 132+Lys 257+Thr 128; Cys 132+Lys 257+Ser 128; Cys 132+Lys 257+Ala 128; Cys 132+Lys 257+Ala 156;

Cys 132+Trp 260+Glu 123; Cys 132+Trp 260+His 134; Cys 132+Trp 260+Arg 134; Cys 132+Trp 260+Thr 128; Cys 132+Trp 260+Ser 128; Cys 132+Trp 260+Ala 128; Cys 132+Trp 260+Ala 156;

Cys 132+Glu 123+His 134; Cys 132+Glu 123+His 134; Cys 132+Glu 123+Arg 134; Cys 132+Glu 123+Thr 128; Cys 132+Glu 123+Ser 128; Cys 132+Glu 123+Ala 128; Cys 132+Glu 123+Ala 156;

Cys 132+His 134+Thr 128; Cys 132+His 134+Ser 128; Cys 132+His 134+Ala 128; Cys 132+His 134+Ala 156;

Cys 132+Arg 134+Thr 128; Cys 132+Arg 134+Ser 128; Cys 132+Arg 134+Ala 128; Cys 132+Arg 134+Ala 156;

Cys 132+Thr 128+Ala 156; Cys 132+Ser 128+Ala 156; Cys 132+Ala 128+Ala 156;

Cys 132+Asp 253+Lys 257+Trp 260; Cys 132+Asp 253+Lys 257+Glu 123; Cys 132+Asp 253+Lys 257+His 134; Cys 132+Asp 253+Lys 257+Arg 134; Cys 132+Asp 253+Lys 257+Thr 128; Cys 132+Asp 253+Lys 257+Ser 128; Cys 132+Asp 253+Lys 257+Ala 128; Cys 132+Asp 253+Lys 257+Ala 156;

Cys 132+Lys 157+Trp 260+Glu 123; Cys 132+Lys 157+Trp 260+His 134; Cys 132+Lys 157+Trp 260+Arg 134; Cys 132+Lys 157+Trp 260+Thr 128; Cys 132+Lys 157+Trp 260+Ser 128; Cys 132+Lys 157+Trp 260+Ala 128; Cys 132+Lys 157+Trp 260+Ala 156;

Cys 132+Trp 260+Glu 123+His 134; Cys 132+Trp 260+Glu 123+Arg 134; Cys 132+Trp 260+Glu 123+Thr 128; Cys 132+Trp 260+Glu 123+Ser 128; Cys 132+Trp 260+Glu 123+Ala 128; Cys 132+Trp 260+Glu 123+Ala 156;

Cys 132+Glu 123+His 134+Thr 128; Cys 132+Glu 123+His 134+Ser 128; Cys 132+Glu 123+His 134+Ala 128; Cys 132+Glu 123+His 134+Ala 156;

Cys 132+Glu 123+Arg 134+Thr 128; Cys 132+Glu 123+Arg 134+Ser 128; Cys 132+Glu 123+Arg 134+Ala 128; Cys 132+Glu 123+Arg 134+Ala 156;

Cys 132+His 134+Thr 128+Ala 156; Cys 132+His 134+Ser 128+Ala 156; Cys 132+His 134+Ala 128+Ala 156;

Cys 132+Arg 134+Thr 128+Ala 156; Cys 132+Arg 134+Ser 128+Ala 156; Cys 132+Arg 134+Ala 128+Ala 156;

Cys 132+Asp 253+Lys 257+Trp 260+Glu 123; Cys 132+Asp 253+Lys 257+Trp 260+His 134; Cys 132+Asp 253+Lys 257+Trp 260+Arg 134; Cys 132+Asp 253+Lys 257+Trp 260+Thr 128; Cys 132+Asp 253+Lys 257+Trp 260+Ser 128; Cys 132+Asp 253+Lys 257+Trp 260+Ala 128; Cys 132+Asp 253+Lys 257+Trp 260+Ala 156;

Cys 132+Lys 257+Trp 260+Glu 123+His 134; Cys 132+Lys 257+Trp 260+Glu 123+Arg 134; Cys 132+Lys 257+Trp 260+Glu 123+Thr 128; Cys 132+Lys 257+Trp 260+Glu 123+Ser 128; Cys 132+Lys 257+Trp 260+Glu 123+Ala 128; Cys 132+Lys 257+Trp 260+Glu 123+Ala 156;

Cys 132+Trp 260+Glu 123+His 134+Thr 128; Cys 132+Trp 260+Glu 123+His 134+Ser 128; Cys 132+Trp 260+Glu 123+His 134+Ala 128; Cys 132+Trp 260+Glu 123+His 134+Ala 156;

Cys 132+Trp 260+Glu 123+Arg 134+Thr 128; Cys 132+Trp 260+Glu 123+Arg 134+Ser 128; Cys 132+Trp 260+Glu 123+Arg 134+Ala 128; Cys 132+Trp 260+Glu 123+Arg 134+Ala 156;

Cys 132+Glu 123+Arg 134+Thr 128+Ala 156; Cys 132+Glu 123+Arg 134+Ser 128+Ala 156; Cys 132+Glu 123+Arg 134+Ala 128+Ala 156;

Cys 132+Glu 123+His 134+Thr 128+Ala 156; Cys 132+Glu 123+His 134+Ser 128+Ala 156; Cys 132+Glu 123+His 134+Ala 128+Ala 156;

Cys 132+Asp 253+Lys 257+Trp 260+Glu 123+His 134; Cys 132+Asp 253+Lys 257+Trp 260+Glu 123+Arg 134; Cys 132+Asp 253+Lys 257+Trp 260+Glu 123+Thr 128; Cys 132+Asp 253+Lys 257+Trp 260+Glu 123+Ser 128; Cys 132+Asp 253+Lys 257+Trp 260+Glu 123+Ala 128; Cys 132+Asp 253+Lys 257+Trp 260+Glu 123+Ala 156;

Cys 132+Lys 257+Trp 260+Glu 123+His 134+Thr 128; Cys 132+Lys 257+Trp 260+Glu 123+His 134+Ser 128; Cys 132+Lys 257+Trp 260+Glu 123+His 134+Ala 128; Cys 132+Lys 257+Trp 260+Glu 123+His 134+Ala 156;

Cys 132+Lys 257+Trp 260+Glu 123+Arg 134+Thr 128; Cys 132+Lys 257+Trp 260+Glu 123+Arg 134+Ser 128; Cys 132+Lys 257+Trp 260+Glu 123+Arg 134+Ala 128; Cys 132+Lys 257+Trp 260+Glu 123+Arg 134+Ala 156;

Cys 132+Trp 260+Glu 123+Arg 134+Thr 128+Ala 156; Cys 132+Trp 260+Glu 123+Arg 134+Ser 128+Ala 156; Cys 132+Trp 260+Glu 123+Arg 134+Ala 128+Ala 156;

Cys 132+Trp 260+Glu 123+His 134+Thr 128+Ala 156; Cys 132+Trp 260+Glu 123+His 134+Ser 128+Ala 156; Cys 132+Trp 260+Glu 123+His 134+Ala 128+Ala 156;

Cys 132+Asp 253+Lys 257+Trp 260+Glu 123+His 134+Thr 128; Cys 132+Asp 253+Lys 257+Trp 260+Glu 123+His 134+Ser 128; Cys 132+Asp 253+Lys 257+Trp 260+Glu 123+His 134+Ala 128; Cys 132+Asp 253+Lys 257+Trp 260+Glu 123+His 134+Ala 156;

Cys 132+Asp 253+Lys 257+Trp 260+Glu 123+Arg 134+Thr 128; Cys 132+Asp 253+Lys 257+Trp 260+Glu 123+Arg 134+Ser 128; Cys 132+Asp 253+Lys 257+Trp 260+Glu 123+Arg 134+Ala 128; Cys 132+Asp 253+Lys 257+Trp 260+Glu 123+Arg 134+Ala 156;

Cys 132+Lys 257+Trp 260+Glu 123+His 134+Thr 128+Ala 156; Cys 132+Lys 257+Trp 260+Glu 123+His 134+Ser 128+Ala 156; Cys 132+Lys 257+Trp 260+Glu 123+His 134+Ala 128+Ala 156;

Cys 132+Lys 257+Trp 260+Glu 123+Arg 134+Thr 128+Ala 156; Cys 132+Lys 257+Trp 260+Glu 123+Arg 134+Ser 128+Ala 156; Cys 132+Lys 257+Trp 260+Glu 123+Arg 134+Ala 128+Ala 156;

Cys 132+Asp 253+Lys 257+Trp 260+Glu 123+His 134+Thr 128+Ala 156; Cys 132+Asp 253+Lys 257+Trp 260+Glu 123+His 134+Ser 128+Ala 156; Cys 132+Asp 253+Lys 257+Trp 260+Glu 123+His 134+Ala 128+Ala 156;

Cys 132+Asp 253+Lys 257+Trp 260+Glu 123+Arg 134+Thr 128+Ala 156; Cys 132+Asp 253+Lys 257+Trp 260+Glu 123+Arg 134+Ser 128+Ala 156; Cys 132+Asp 253+Lys 257+Trp 260+Glu 123+Arg 134+Ala 128+Ala 156.

However, in the above list, Cys 132 may also be substituted by either Ser 132, Glu 132, Asp 132, or Thr 132.

In general, the retinal or retinal derivative necessary for the functioning of the light-inducible ion channel is produced by the cell to be transfected with said ion channel. Depending on its conformation, the retinal may be all-trans retinal, 11-cis-retinal, 13-cis-retinal, or 9-cis-retinal. However, it is also contemplated that the mutant light-inducible ion channel of the invention may be incorporated into vesicles, liposomes or other artificial cell membranes. Accordingly, in a second aspect, the invention provides a channelrhodopsin, comprising the light-inducible ion channel according to the first aspect and a retinal or retinal derivative. Preferably, the retinal derivative is selected from the group consisting of 3,4-dehydroretinal, 13-ethylretinal, 9-dm-retinal, 3-hydroxyretinal, 4-hydroxyretinal, naphthylretinal; 3,7,11-trimethyl-dodeca-2,4,6,8,10-pentaenal; 3,7-dimethyl-deca-2,4,6,8-tetraenal; 3,7-dimethyl-octa-2,4,6-trienal; and 6-7 rotation-blocked retinals, 8-9 rotation-blocked retinals, and 10-11 rotation-blocked retinals. In addition, the preferred embodiments of the first aspect correspond to the preferred embodiments of the second aspect.

In a third aspect, the invention also relates to a nucleic acid construct, comprising a nucleotide sequence coding for the light-inducible ion channel according to the first aspect. To ensure optimal expression, the coding DNA can also be suitably modified, for example by adding suitable regulatory sequences and/or targeting sequences and/or by matching of the coding DNA sequence to the preferred codon usage of the chosen host. The targeting sequence may encode a C-terminal extension targeting the light-inducible ion channel to a particular site or compartment within the cell, such as to the synapse or to a post-synaptic site, to the axon-hillock, or the endoplasmic reticulum. The nucleic acid may be combined with further elements, e.g., a promoter and a transcription start and stop signal and a translation start and stop signal and a polyadenylation signal in order to provide for expression of the sequence of the protein of the invention. The promoter can be inducible or constitutive, general or cell specific promoter. An example of a cell-specific promoter is the mGlu6-promotor specific for bipolar cells. Selection of promoters, vectors and other elements is a matter of routine design within the level of ordinary skill in the art. Many such elements are described in the literature and are available through commercial suppliers.

Accordingly, in a fourth aspect, the invention provides an expression vector, comprising a nucleotide sequence coding for the light-inducible ion channel according to the first aspect or the nucleic acid construct according to the third aspect. In a preferred embodiment, the vector is suitable for gene therapy, in particular wherein the vector is suitable for virus-mediated gene transfer. The term "suitable for virus-mediated gene transfer" means herein that said vector can be packed in a virus and thus be delivered to the site or the cells of interest. Examples of viruses suitable for gene therapy are retroviruses, adenoviruses, adeno-associated viruses, lentiviruses, pox viruses, alphaviruses, rabies virus, semliki forest virus and herpes viruses. These viruses differ in how well they transfer genes to the cells they recognize and are able to infect, and whether they alter the cell's DNA permanently or temporarily. However, gene therapy also encompasses non-viral methods, such as application of naked DNA, lipoplexes and polyplexes, and dendrimers.

As described above, the resulting nucleic acid sequence may be introduced into cells e.g. using a virus as a carrier or by transfection including e.g. by chemical transfectants (such as Lipofectamine, Fugene, etc.), electroporation, calcium phosphate co-precipitation and direct diffusion of DNA. A method for transfecting a cell is detailed in the examples and may be adapted to the respective recipient cell. Transfection with DNA yields stable cells or cell lines, if the transfected DNA is integrated into the genome, or unstable (transient) cells or cell lines, wherein the transfected DNA exists in an extrachromosomal form. Furthermore, stable cell lines can be obtained by using episomal replicating plasmids, which means that the inheritance of the extrachromosomal plasmid is controlled by control elements that are integrated into the cell genome. In general, the selection of a suitable vector or plasmid depends on the intended host cell.

Therefore, in a fifth aspect, the invention relates to a cell comprising the channelrhodopsin according to the second aspect, the nucleic acid construct according to the third aspect or the expression vector according to the fourth aspect.

As it will be described below, one application of the mutant light-inducible ion channel according to the present invention is the treatment of blind subjects such as humans or animals. There are a number of diseases in which the natural visual cells no longer function, but all nerve connections are capable of continuing to operate. Today, attempts are being made in various research centres to implant thin films with artificial ceramic photocells on the retina. These photocells are intended to depolarise the secondary, still intact cells of the retinal and thereby to trigger a nerve impulse (bionic eyes). The deliberate expression of light-controlled ion channels according to the invention in these ganglion cells, amacrine cells or bipolar cells would be a very much more elegant solution and enable greater three-dimensional visual resolution.

The incorporation of the mutant light-inducible ion channel into the membrane of cells which do not express the corresponding channels in nature can for example be simply effected in that, using known procedures of recombinant DNA technology, the DNA coding for this ion channel is firstly incorporated into a suitable expression vector, e.g. a plasmid, a cosmid or a virus, the target cells are then transformed with this, and the protein is expressed in this host.

Next, the cells are treated in a suitable manner, e.g. with retinal, in order to enable the linkage of a Schiffs base between protein and retinal.

In a preferred embodiment, this occurs in various yeasts such as *Saccharomyces cerevisiae, Schizosaccharo-myces pombe* or *Pichia pastoris* as already successfully performed for rhodopsins such as bacteriorhodopsin and/or bovine rhodopsin.

The expression can also be effected in certain mammalian cell systems or insect cell systems. Thus, in a preferred embodiment, the cell is a mammalian cell or an insect cell. The expression is effected either with episomal vectors as transient expression, preferably in melanoma cells (e.g., the BLM cell line), COS cells (generated by infection of "African green monkey kidney CV1" cells) or HEK cells ("human embryonic kidney cells", e.g. HEK293 cells), or BHK-cells ("baby hamster kidney cells"), or in the form of stable expression (by integration into the genome) in CHO cells ("Chinese hamster ovary cells"), myeloma cells or MDCK cells ("Madine-Darby canine kidney cells") or in Sf9 insect cells infected with baculoviruses. Accordingly, in a more preferred embodiment the mammalian cell is a COS cell; a BHK cell; a HEK293 cell; a CHO cell; a myeloma cell; or a MDCK cell.

In the context of restoring vision, in a most preferred embodiment, the mammalian cell is a photoreceptor cell; a retinal rod cell; a retinal cone cell; a retinal ganglion cell; a bipolar neuron; a ganglion cell; a pseudounipolar neuron; a multipolar neuron; a pyramidal neuron, a Purkinje cell; or a granule cell.

A neuron is an electrically excitable cell that processes and transmits information by electrical and chemical signalling, wherein chemical signaling occurs via synapses, specialized connections with other cells. A number of specialized types of neurons exist such as sensory neurons responding to touch, sound, light and numerous other stimuli affecting cells of the sensory organs, motor neurons receiving signals from the brain and spinal cord and causing muscle contractions and affecting glands, and interneurons connecting neurons to other neurons within the same region of the brain or spinal cord. Generally, a neuron possesses a soma, dendrites, and an axon. Dendrites are filaments that arise from the cell body, often extending for hundreds of microns and branching multiple times. An axon is a special cellular filament that arises from the cell body at a site called the axon hillock. The cell body of a neuron frequently gives rise to multiple dendrites, but never to more than one axon, although the axon may branch hundreds of times before it terminates. At the majority of synapses, signals are sent from the axon of one neuron to a dendrite of another. There are, however, many exceptions to these rules: neurons that lack dendrites, neurons that have no axon, synapses that connect an axon to another axon or a dendrite to another dendrite, etc. Most neurons can further be anatomically characterized as unipolar or pseudounipolar (dendrite and axon emerge from same process), bipolar (axon and single dendrite on opposite ends of the soma), multipolar (having more than two dendrites and may be further classified as (i) Golgi I neurons with long-projecting axonal processes, such as pyramidal cells, Purkinje cells, and anterior horn cells, and (ii) Golgi II: neurons whose axonal process projects locally, e.g., granule cells.

A photoreceptor cell, is a specialized neuron found in the retina that is capable of phototransduction. The two classic photoreceptors are rods and cones, each contributing information used by the visual system. A retinal ganglion cell is a type of neuron located near the inner surface of the retina of the eye. These cells have dendrites and long axons projecting to the protectum (midbrain), the suprachiasmatic nucleus in the hypothalamus, and the lateral geniculate (thalamus). A small percentage contribute little or nothing to vision, but are themselves photosensitive. Their axons form the retinohypothalamic tract and contribute to circadian rhythms and pupillary light reflex, the resizing of the pupil. They receive visual information from photoreceptors via two intermediate neuron types: bipolar cells and amacrine cells. Amacrine cells are interneurons in the retina, and responsible for 70% of input to retinal ganglion cells. Bipolar cells, which are responsible for the other 30% of input to retinal ganglia, are regulated by amacrine cells. As a part of the retina, the bipolar cell exists between photoreceptors (rod cells and cone cells) and ganglion cells. They act, directly or indirectly, to transmit signals from the photoreceptors to the ganglion cells.

The cell may be isolated (and genetically modified), maintained and cultured at an appropriate temperature and gas mixture (typically, 37° C., 5% CO2), optionally in a cell incubator as known to the skilled person and as exemplified for certain cell lines or cell types in the examples. Culture conditions may vary for each cell type, and variation of conditions for a particular cell type can result in different phenotypes. Aside from temperature and gas mixture, the most commonly varied factor in cell culture systems is the growth medium. Recipes for growth media can vary in pH, glucose concentration, growth factor and the presence of other nutrient components among others. Growth media are either commercially available, or can be prepared according to compositions, which are obtainable from the American Tissue Culture Collection (ATCC). Growth factors used for supplement media are often derived from animal blood such as calf serum. Additionally, antibiotics may be added to the growth media. Amongst the common manipulations carried out on culture cells are media changes and passaging cells.

There are additional potential fields of application for CatCh. Since $Ca^{++}$ is an important intracellular regulator, CatCh opens the doors to optical intervention into the fine-tuned $Ca^{++}$ homeostasis of the cell, modulating its state and activity. In basic research, CatCh may be used to optically control $Ca^{++}$-dependent exocytosis as an alternative to caged $Ca^{++26}$ (e.g. transmitter release at the synapse), to optically activate downstream intracellular processes via calcium-activated kinases and phosphatases or to induce apoptosis by targeting CatCh to intracellular compartments such as the Golgi apparatus or endoplasmatic reticulum.

Therefore, a further aspect of the invention is the use of the light-inducible ion channel according to the first aspect or channelrhodopsin according to the second aspect, or the nucleic acid construct according to the third aspect, or the cell according to the invention as a medicament. In particular, the expression vector of the invention may be used in gene therapy. More specifically, the light-inducible ion channel according to the first aspect, channelrhodopsin according to the second aspect, nucleic acid construct according to the third aspect, or the cell according to the invention may be used in the treatment of blindness or reduced sight. However, due to its fast spike onset of action of up to 300 Hz and accelerated repolarisation, a use of the light-inducible ion channel in the re-establishing of hearing or the treatment of deafness is also contemplated.

Additionally, the mutant light-inducible ion channel according to the first aspect may comprise additional substitutions (so called SFO's, or slow mutants, see Table 1), which lead to a permanent light-induced calcium-influx, which in turn leads to cell death. Accordingly, a use of the light-inducible ion-channel according to the invention additionally having threonine, serine, or alanine at a position corresponding to position 128 of SEQ ID NO: 1; and/or alanine at a position corresponding to position 156 of SEQ ID NO: 1 in the ablation of cancer cells is contemplated. For example, the expression vector according to the invention could be targeted by virus-mediated gene transfer via a cancer cell surface marker to cancer cells. Further, it is noted that in particular retroviruses preferably integrate into fast dividing cells, such as cancer cells. As a consequence, the light-inducible ion channel according to the present invention is predominantly expressed and incorporated into the cell membrane of cancer cells. Upon stimulation by light, these ion channels will open and induce a permanent calcium-influx, thereby leading to the death of the cancer cell. Such a use is particularly advantageous in the ablation of cancer cells which are naturally exposed to light, such as a melanoma cancer cells. Therefore, in a preferred embodiment, the cancer is a melanoma cancer.

In a final aspect, the invention pertains to a use of a light-inducible ion channel according to the first aspect, or a channelrhodopsin according to the second aspect, or a cell according to the invention in a high-throughput screening. A high-throughput screening (HTS), is a method for scientific experimentation especially used in drug discovery and relevant to the fields of biology and chemistry. HTS allows a researcher to effectively conduct millions of biochemical, genetic or pharmacological tests in a short period of time, often through a combination of modern robotics, data processing and control software, liquid handling devices, and sensitive detectors. By this process, one may rapidly identify active agents which modulate a particular biomolecular pathway; particularly a substance modifying an ion channel, such as the light-inducible ion channel according to the invention, a $Ca^{++}$-inducible potassium channel, or a BK channel. For example, one might co-express the $Ca^{++}$-inducible potassium channel and the light-inducible ion channel in a host cell. Upon stimulation by light, the light-inducible channel will open and the intracellular $Ca^{++}$ concentration will increase, thereby activating the potassium channel. Thus, one will receive a change in the membrane potential, which may be monitored by potential-sensitive dyes such as RH 421 (N-(4-Sulfobutyl)-4-(4-(4-(dipentylamino)phenyl)butadienyl)pyridinium, inner salt). Such a HTS may thus comprise the following steps: (i) contacting a cell expressing a $Ca^{++}$-inducible (potassium) channel and the light-inducible ion channel according to the invention with a candidate agent directed against the $Ca^{++}$-inducible channel, (ii) applying a light stimulus in order to induce the light-inducible channel, (iii) determining the alteration of the membrane potential (mixed signal), and (iv) comparing the signal determined in step (iii) with the signal determined in a cell only expressing the light-inducible ion channel according to the invention subjected to step (ii) (single signal). A reduction in the change of the membrane potential would be indicative of a promising modulator of the $Ca^{++}$-inducible (potassium) channel. Such an approach is supposed to yield a signal-to-noise ratio of approximately 5:1, which is quite improved compared to direct measurements conducted on a cell only expressing the $Ca^{++}$-inducible channel. Due to the improved signal-to-noise ratio, said method, in particular by using the light-inducible ion channel, may be particularly suitable for HTS.

In essence, HTS uses an approach to collect a large amount of experimental data on the effect of a multitude of substances on a particular target in a relatively short time. A screen, in this context, is the larger experiment, with a single goal (usually testing a scientific hypothesis), to which all this data may subsequently be applied. For HTS cells according to the invention may be seed in a tissue plate, such as a multi well plate, e.g. a 96-well plate. Then the cell in the plate is contacted with the test substance for a time sufficient to interact with the targeted ion channel. The test substance may be different from well to well across the plate. After incubation time has passed, measurements are taken across all the plate's wells, either manually or by a machine and optionally compared to measurements of a cell which has not been contacted with the test substance. Manual measurements may be necessary when the researcher is using patch-clamp, looking for effects not yet implemented in automated routines. Otherwise, a specialized automated analysis machine can run a number of experiments on the wells (such as analysing light of a particular frequency or a high-throughput patch-clamp measurement). In this case, the machine outputs the result of each experiment e.g. as a grid of numeric values, with each number mapping to the value obtained from a single well. Depending upon the results of this first assay, the researcher can perforin follow up assays within the same screen by using substances similar to those identified as active (i.e. modifying an intracellular cyclic nucleotide level) into new assay plates, and then re-running the experiment to collect further data, optimize the structure of the chemical agent to improve the effect of the agent on the cell. Automation is an important element in HTS's usefulness. A specialized robot is often responsible for much of the process over the lifetime of a single assay plate, from creation through final analysis. An HTS robot can usually prepare and analyze many plates simultaneously, further speeding the data-collection process. Examples for apparatuses suitable for HTS in accordance with the present invention comprise a Fluorometric Imaging Plate Reader (FLIPR™; Molecular Devices), FLEXstation™ (Molecular Devices), Voltage Ion Probe Reader (VIPR, Aurora Biosciences), Attofluor® Ratio Vision® (ATTO).

In the following, the present invention is illustrated by figures and examples which are not intended to limit the scope of the present invention.

EXAMPLES

Construction and Biophysical Characterization of CatCh

Figure 1:
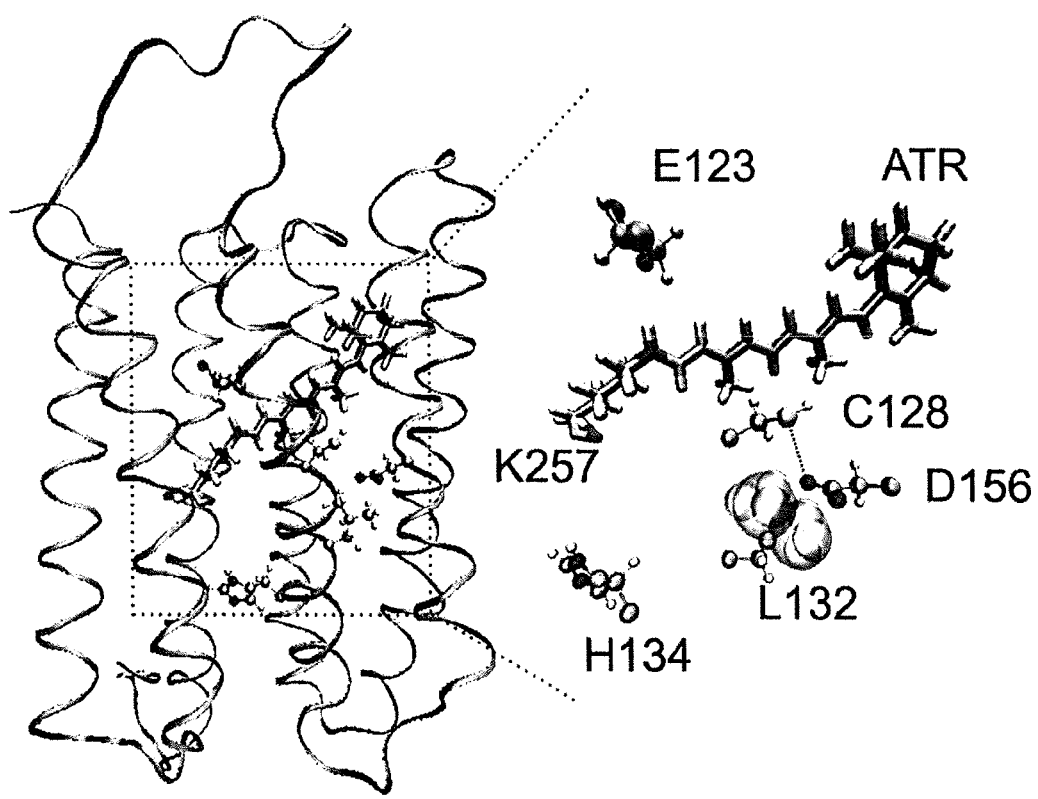
FIG. 1 Homology model of ChR2 based on the Sensory Rhodopsin 2 structure (PDB code 1H2S). The target region for the cysteine scanning (R115 to T139) is located in the transmembrane helix 3 (TM3) and is highlighted in red. The inset shows the presumable location of the mutated L132C, the hydrogen-bonded C128 and D156, connecting TM3 and TM4 as indicated by the dotted line, and the homologue residues for the proton donor (H134) and proton acceptor (E123), respectively. The chromophore is formed by all-trans retinal (ATR) and K257 covalently linked by a Schiff-base. The cavity formed by the removal of the leucins's methyl groups is depicted as spheres and overlaid on the mutated sulfhydryl group of the cysteine residue (yellow ball). The figure was prepared with VMD[30].

In contrast to previous approaches, the inventors' objective was to identify residues within WT ChR2 whose mutations modify cation permeability. The inventors focused on the third transmembrane domain as several mutated residues within this domain have been shown to alter the photocycle and the gating of the channel (FIG. 1)[5-7,12]. Each residue from Arg$^{115}$ to Thr$^{139}$ was individually replaced by cysteine and screened for functional changes in *Xenopus laevis* oocytes.

Spectroscopy.

CatCh was expressed in and purified from *Pichia pastoris* as described before[5,13]. Flash-photolysis studies were performed and absorbance changes were measured after excitation of a 10 ns laser flash from an excimer pumped dye laser (450 nm, 2-3 mJ)[13].

The L132C (CatCh) mutation displays significant alterations in the amplitude and shape of the current traces.

HEK293 Cell Culture and Molecular Biology.

C-terminally truncated ChR2(L132C)-YFP (vector: pcDNA3(−)-chop2-309-(L132C)-EYFP) was transfected in HEK293 cells and kept under G418 selection at all times (0.6 mg/ml; PAA Germany, Cölbe, Germany). For the wild-type WT ChR2, the C-terminally truncated ChR2-YFP (vector: pcDNA4TO-chop2-309-EYFP) was stably transfected into HEK293-Trex cells (Invitrogen), cultured and induced as described[13]. The peak to stationary relations were determined from HEK293 cells transiently transfected (Effectene, QIAGEN) with human-codon-optimized pcDNA3.1(−)-ChR2-YFP constructs (WT, H134R or L132C) 24 hours prior to measurements.

Electrophysiological Recordings on HEK293 Cells.

Patch pipettes with resistances of 2-4 MΩ were fabricated from thin-walled borosilicate glass (GB150-8P, Science Products, Hofheim, Germany) on a horizontal DMZ-Universal puller (Serial No. 5318904120B, Zeitz-Instruments, Augsburg, Germany). Photocurrents were recorded with the whole-cell patch-clamp method and activated by light pulses from a diode-pumped solid-state laser (Pusch Opto Tech GmbH, Baden Baden, Germany; λ=473 nm) focused into a 400 μm optic fiber. Light pulses were applied by a fast computer-controlled shutter (Uniblitz LS6ZM2, Vincent Associates). All light intensities given are measured at the end of the light-guide. To get an estimate of the permeability for different cations, we measured photocurrent-voltage relationships and determined the reversal potential. The intracellular solution contained 140 mM NaCl, 7 mM EGTA, 2 mM $MgCl_2$ and 10 mM Tris (pH=9) and the extracellular solution contained 140 mM NaCl, 2 mM $MgCl_2$ and 10 mM Tris (pH=9). For cation permeabilities, external 140 mM NaCl was exchanged by 140 mM KCl, 90 mM $CaCl_2$ or 90 mM $MgCl_2$, respectively. Proton permeabilities were determined from the reversal potential shift of the current-voltage-relationship when the pH was reduced from 9 to 7.4 (or 6). Permeability ratios were calculated according to the Goldman-Hodgkin-Katz (GHK) equation, including terms for $Na^+$, $K^+$, $H^+$ and $Ca^{++}$.

Figure 2:
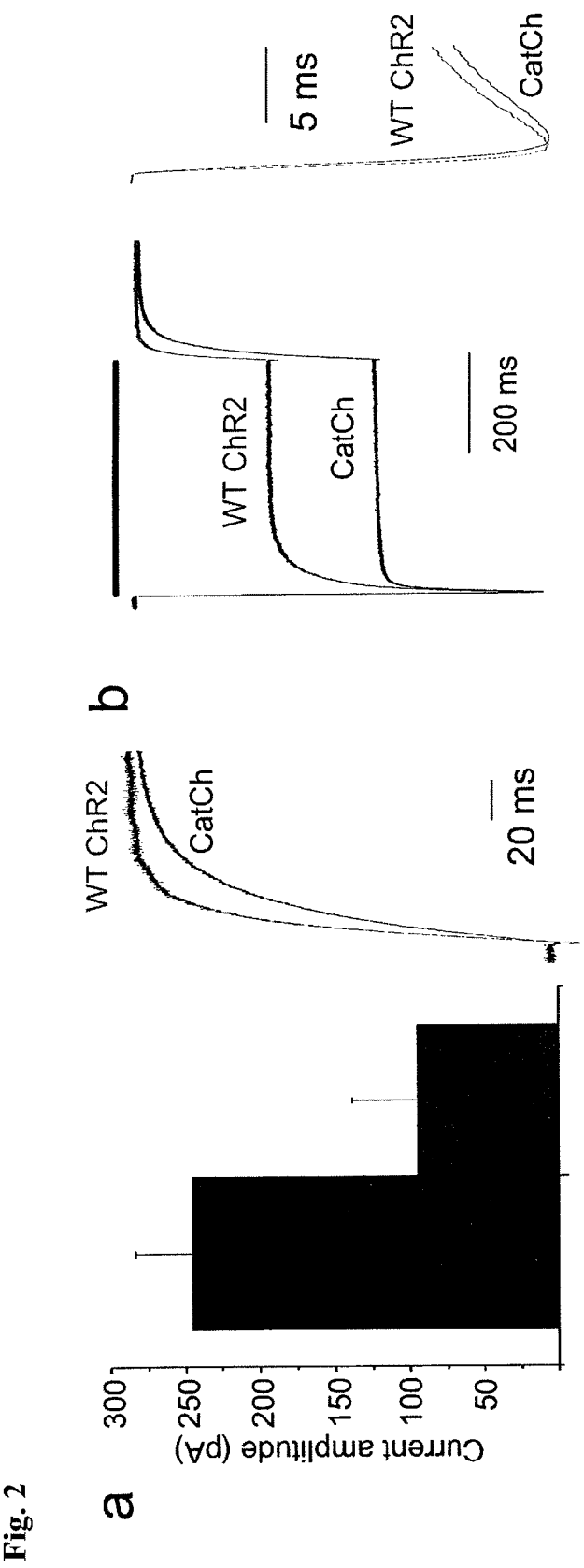
FIG. 2 Biophysical characterization of CatCh in HEK293 cells and *Xenopus* oocytes. (a) Left, summary of steady-state current amplitudes in response to 500 ms blue light pulses measured in HEK293 cells at –60 mV expressing CatCh (black) and WT ChR2 (red), shown as mean±s.d. (n=6). Right, comparison of off-kinetics of photocurrents normalized to steady-state currents. (b) Left, actual photocurrents in response to 1-s blue 473-nm light pulses. Traces are normalized to the peak photocurrent amplitude to illustrate the increase in the steady state-to-peak current ratio in CatCh (black) compared to the WT (red). Right, comparison of on-kinetics of photocurrents normalized to peak currents. (c) 473-nm light responses of CatCh and WT ChR2 expressing *Xenopus* oocytes in 80 mM extracellular $Ca^{++}$ (pH 9) at –120 mV (continuous lower traces). Injection of the $Ca^{++}$ chelator BAPTA to a final cytosolic concentration of 1 mM abolished the superimposed currents of the intrinsic $Ca^{++}$-activated chloride channels, while residual channelrhodopsin $Ca^{++}$-currents remained (dashed upper traces). Currents were normalized to the WT ChR2 peak current and are typical of six other experiments. Notice the larger photocurrent amplitude difference before and after BAPTA injection of CatCh, indicating its increased $Ca^{++}$ permeability compared to WT ChR2. (d) Ion flux characteristics of CatCh in HEK293 cells at −80 mV (n=6, see methods). (e) Current-voltage relationships of WT ChR2 (-■-) and CatCh (-▲-) in 90 mM $CaCl_2$ compared to 140 mM NaCl (-●-, WT ChR2 and CatCh superimposed). Currents normalized to WT ChR2 current at −100 mV. The reversal potential of CatCh in $CaCl_2$ is shifted to positive potentials, indicating an increased $Ca^{++}$-permeability (mean±s.d., n=5). (f) Fura-2 measurements of $Ca^{++}$-influx in HEK293 cells expressing WT ChR2 (●) and CatCh (■) to 10 s of 460 nm light (blue bar) in the presence of 90 mM extracellular $Ca^{++}$ (n=10) showing four-fold increased elevation of intracellular $Ca^{++}$ in CatCh (control untransfected HEK293 cells, ▲).
Figure 2:
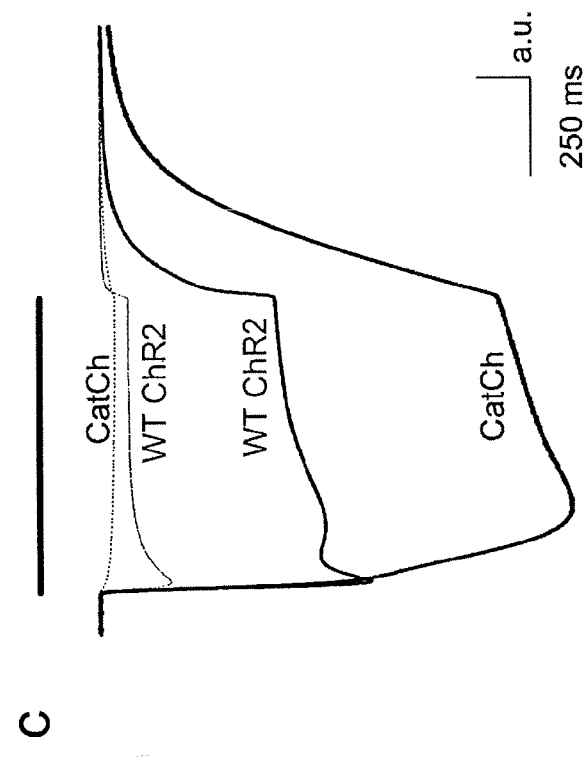
Figure 2:
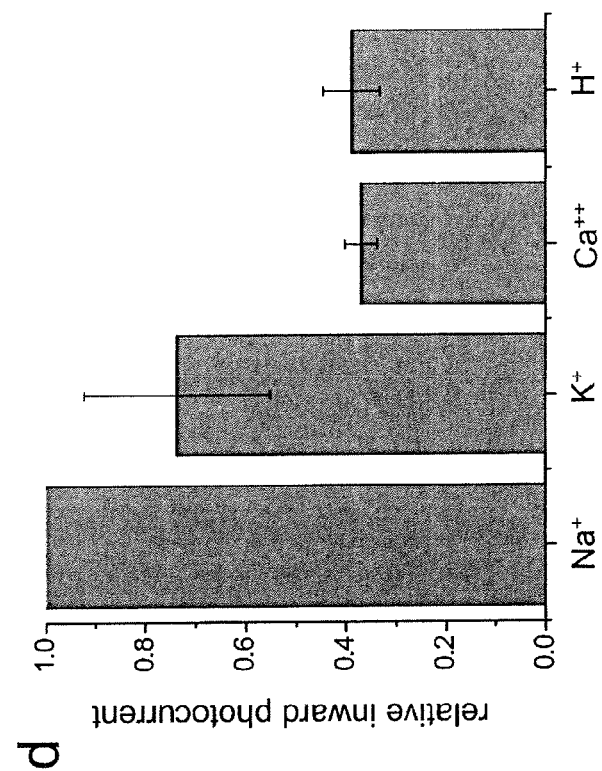
Figure 2:
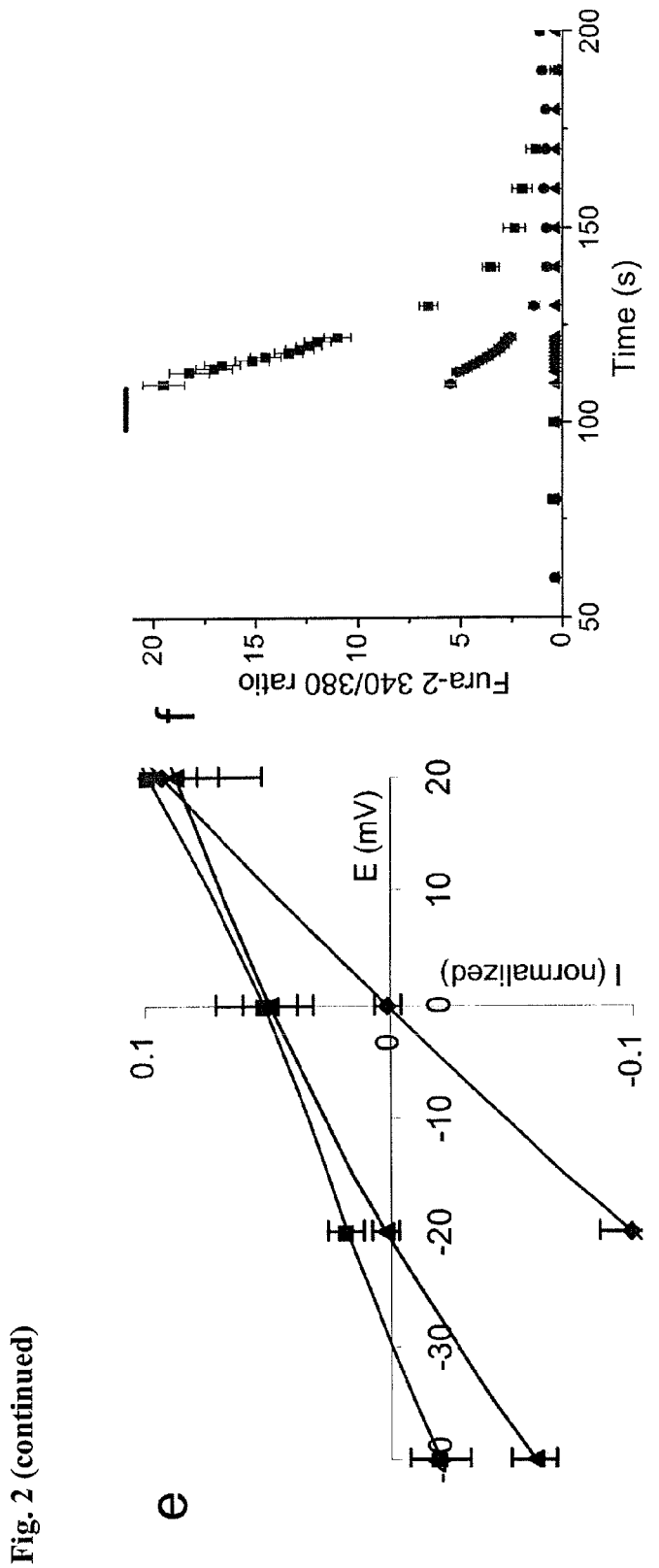
Figure 5:
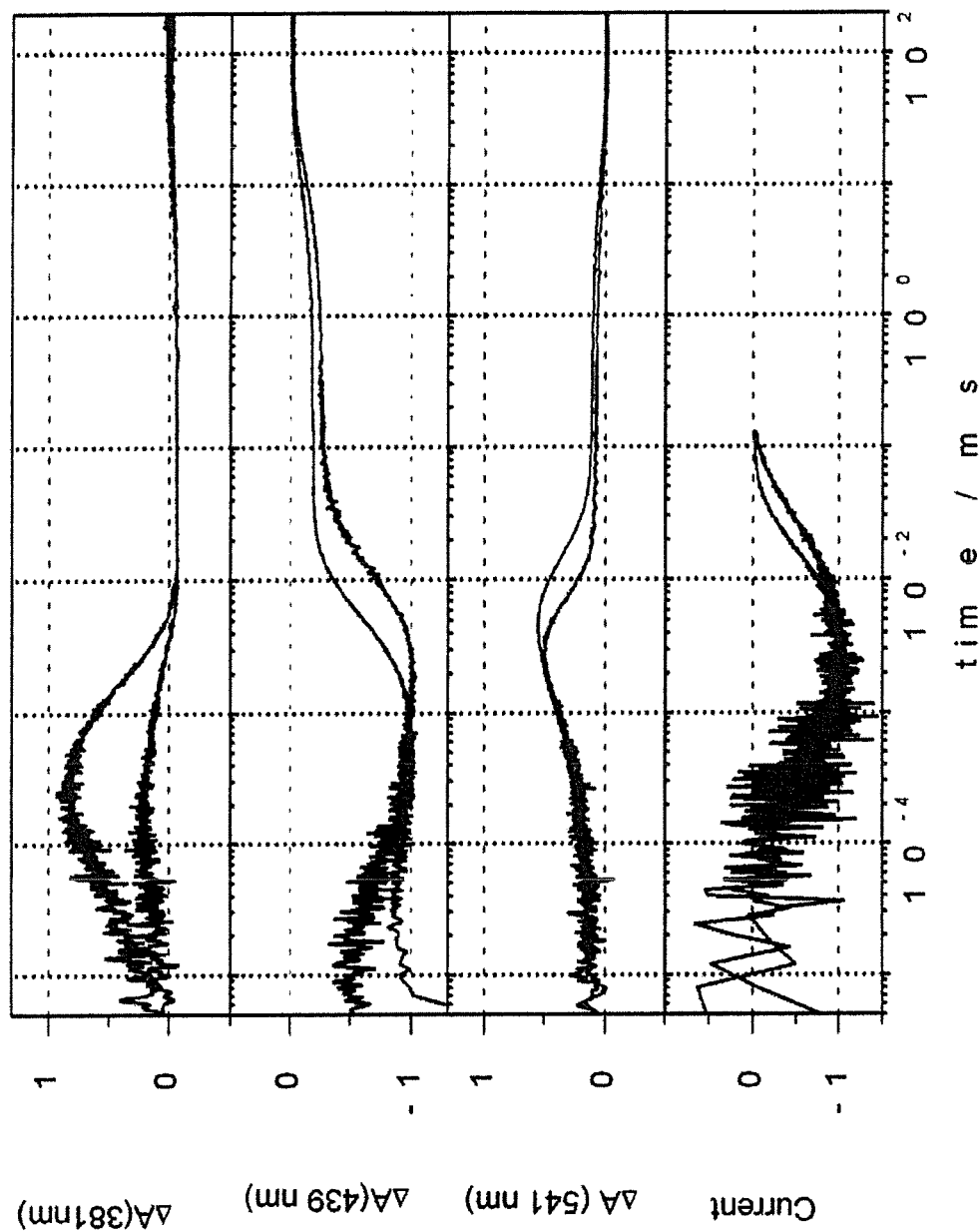
FIG. 5 Spectroscopic characterization of CatCh. After light excitation, the CatCh (black traces) mutant enters a photocycle comparable to the WT (red traces) in kinetics and in the presence of photointermediates. The figure depicts the spectral changes after 450 nm excitation with the characteristic wavelengths for the deprotonated Schiff-base, P390 (381 nm, top panel), for P520, dominant in the open state (541 nm, second panel), and the ground state (440 nm, third panel). The first red-shifted intermediate, presumably P500, is not resolved and only detected as offset. The Schiff-base deprotonates in the microsecond time scale (τ=50 μs), an event that is hardly observable due to the low amplitude at 381 nm, concomitant with a rise at 541 nm. The rise of the P520 intermediate occurs in the following process (t=1.5 ms), before it decays (t=9 ms) thereby populating a second lasting species (P480). The ground state (D470) reverts in the following process (t=10 s). The transitions in the photocycle resemble those observed in the WT. As for the opening and the closing kinetics in the current measurements, the mutation causes no gross change in the functional states. The open state is determined mainly by the P520 intermediate. The main difference is found in the extent of the P390 amplitude compared to P520 that is lower than in the WT. Therefore, the L132C mutation does not affect the light reaction at the chromophore site. Note that the spectroscopic kinetics data of the photocycle was not altered in the presence of 50 mM $Ca^{++}$.

In HEK293 cells, the blue light induced stationary currents of CatCh had a ~2.5-fold higher amplitude compared to WT ChR2 24 h after transfection (CatCh: 25.0±8.8 pA/pF; WT: 10.1±4.1 pA/pF; mean±s.d., n=6, −60 mV, FIG. 2a). The steady-state to peak-current ratio also increased from 0.37±0.18 in the WT to 0.71±0.16 in CatCh (FIG. 2b). During repetitive blue-light stimulation the CatCh peak current disappeared. It recovered within minutes in the dark, when recovery was not prematurely induced by yellow light. In contrast, a full recovery of the WT ChR2 peak current under identical conditions takes 20 seconds[13]. Activation and deactivation time constants of CatCh ($\tau_{on}$=590±3 μs, $\tau_{off}$=15±2 ms, n=9, pH 7.4, −60 mV, mean±s.d.) were slightly longer compared to WT ChR2 ($\tau_{on}$=214±2 μs, $\tau_{off}$=10±1 ms, n=9, pH 7.4, −60 mV; mean±s.d.; FIGS. 2a,b, FIG. 5 bottom panel, table 1).

Next, the inventors compared the described effects on the channel properties to the spectral changes in the photocycle. Flash photolysis experiments on purified CatCh revealed only minor deviations from the WT ChR2 spectra[13] (see FIG. 5). 1. The early P390 intermediate, which represents the deprotonated Schiff base, is barely detectable. 2. The intermediate P520, which represents the open state of the channel, shows a slightly lengthened life-time of 9 ms, comparable to the $\tau_{off}$ value determined electrophysiologically. Similar open life-time values were obtained for the mutant H134R, which showed doubled activity at unchanged unit conductance[2,14]. Therefore, also in the case of CatCh, the decelerated kinetics of the open state could be responsible for the 2.5-fold increased stationary currents measured in HEK293 cells, whereby the unit conductance remains unchanged. This was confirmed by measuring the single channel conductance of CatCh using stationary noise analysis as previously described[14].

Noise Analysis.

Experiments were performed on HEK293 cells as described previously[14] and conducted at room temperature (23° C.). The pipette solution contained 1 mM Guanidine-HCl, 199 mM NMG-Cl (N-Methylglucamine), 10 mM EGTA, 2 mM $MgCl_2$, and 20 mM Hepes (pH 7.4), the bath solution contained 200 mM guanidine-HCl, 2 mM $MgCl_2$, 2 mM $CaCl_2$, and 20 mM Hepes (pH 7.4). Current response to a blue light stimulus was recorded under application of a voltage step protocol under saturating light conditions and again under light conditions where the current response at −60 mV was half the maximal current ($I_{0.5}$; 2 kHz low-pass Bessel filter; sampling rate: 100 kHz; cell diameter: 15 μm). Recordings of the stationary $I_{0.5}$ during prolonged illumination (2 min) at −60 mV holding potential were used to estimate the conductance of the single channel (2 kHz low-pass Bessel filter; sampling rate 20 kHz). Alternating recordings without (control, 3 recordings) and with illumination (2 recordings, 30 sec after the onset of the light stimulus) were collected, Fourier transformed and the single channel conductance estimated from an approximation with a Lorentzian function (for details see[14]). The lower light intensities were chosen in order to obtain the maximal fluctuation of the opening and closing of the light-gated channel.

In line with the WT ChR2 and H134R noise analysis experiments, guanidine was used as conducting ion. Note that the kinetic properties of the channel are independent on the permeating cation[14]. The evaluation of difference power spectra yielded a single channel conductance γ of 140±5 fS (n=6, −60 mV) for 200 mM guanidine at room temperature (23° C.), which is similar to the extrapolated room temperature WT ChR2 single channel conductance of 150 fS[14]. The open probability of CatCh determined from the noise analysis is unchanged in comparison to H134R ($P_o$~0.6). Thus, an increased open channel life-time can easily account for the observed increase in photocurrents by a factor of 2.5, however, a slightly enhanced expression of CatCh copies cannot be excluded.

*Xenopus laevis* oocyte Preparation and Molecular Biology.

A C-terminally-truncated ChR2 variant (residues 1-315) without extracellularly exposed cysteine residues (containing mutations C34A and C36A) were subcloned into the vector pTLN[27]. Single cysteine mutations were introduced by QuickChange Site-Directed Mutagenesis (Stratagene) and verified by sequencing. The mRNA was prepared using the SP6 mMessage mMachine kit (Ambion, Austin, Tex.). 50 nl cRNA, which included 30 ng of WT ChR2/CatCh mRNA were injected into each *Xenopus* oocyte. Oocytes were obtained by collagenase treatment after partial ovarectomy. After cRNA injection, oocytes were incubated in all-trans retinal (1 from a 1 mM stock in ethanol) and were kept in ORI buffer (90 mM NaCl, 2 mM KCl, 2 mM CaCl$_2$ and 5 mM Mops, pH 7.4) containing 1 mg/ml gentamycin at 18° C. for two to four days.

Two-Electrode-Voltage Clamp on *Xenopus laevis* Oocytes.

Photocurrents were activated with a 75-W xenon arc lamp and a 450±25 nm band filter, the light of which was coupled into a 1-mm-light-guide with an output of ~10$^{18}$ photons s$^{-1}$ cm$^{-2}$. Action spectra were recorded using narrow bandwidth filters (398-645 nm; ±10 nm; K-series Balzer) in combination with neutral density filters to achieve a fiber output of ~1.4× 10$^{17}$ photons s$^{-1}$ cm$^{-2}$ for each wavelength. For action spectra generation, Ca$^{++}$ in the ORI solution was replaced by Ba$^{++}$ to suppress CaCC currents. Current amplitudes at each wavelength were normalized to represent equal photon exposure. The ground spectrum determined by spectroscopy was then fitted to the averaged data points. To suppress calcium-activated chloride channel (CaCC) activation, 50 nl of a 20 mM solution of the fast Ca$^{2+}$-chelator 1,2-bis(2-aminophenoxy) ethane-N,N,N',N'-tetraacetate (BAPTA) was injected into each oocyte (~1 mM final concentration in the oocyte).

Figure 6:
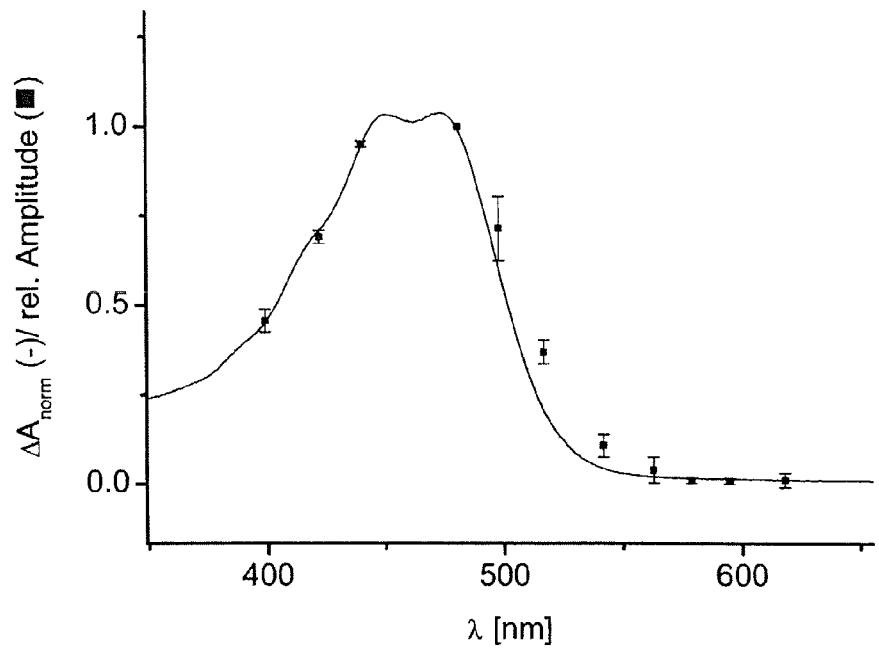
FIG. 6 Action spectrum of CatCh determined by two-electrode-voltage-clamp in *Xenopus* oocytes. Current amplitudes were measured at different wavelengths (λ) in the absence of $Ca^{++}$ (as indicated in the examples), normalized to the photon flux (n=6). Comparison of the ground state (−) and the action spectrum (■).

Excitation of CatCh with varying wavelengths in *Xenopus laevis* oocytes revealed an almost identical action spectrum almost identical to the WT ChR2 spectrum with a maximum excitation wavelength at 474 nm (FIG. 6). In the presence of extracellular Ca$^{++}$ and at negative holding potentials, CatCh currents showed a dramatic increase in amplitude during illumination due to a superimposed outward current which resembles that of calcium activated chloride channels (CaCC) [15,16] (FIG. 2c). In WT ChR2-expressing oocytes CaCC currents were also observed, but they were markedly smaller than those induced by CatCh (FIG. 2c). For both, WT ChR2 and CatCh, at 80 mM extracellular Ca$^{++}$, injection of the fast Ca$^{++}$ chelator BAPTA 1,2-bis(2-aminophenoxy)ethane-N,N, N',N'-tetraacetate into the cell abolished the CaCC currents, while a residual Ca$^{++}$ current remained (FIG. 2c)[1]. The larger difference of the photocurrents before and after BAPTA injection for CatCh supports the hypothesis of an increased Ca$^{++}$ flux following catch activation.

Increased Calcium Permeability of CatCh.

In order to obtain an estimate of the CatCh ion permeability, photocurrent-voltage relationships and the reversal potential for different cations were measured in HEK293 cells. These experiments revealed that the permeabilities for sodium, potassium and magnesium are comparable to WT ChR2 (FIG. 2d)[1]. The proton permeability of CatCh ($p_H/p_{Na}=4*10^6$) is slightly increased compared to WT ChR2 ($p_H/p_{Na}=2.5*10^6$). The Ca$^{++}$-permeability ($p_{Ca}/p_{Na}$) was determined by the reversal potential shift when the 140 mM Na$^+$ of the extracellular solution were replaced by 90 mM Ca$^{++}$. The relative Ca$^{++}$-permeability of CatCh was increased from 0.15 in WT ChR2 to 0.24 as evidenced from the reversal potential (bi-ionic potential) shifting from −30.7±2.7 mV (WT ChR2, mean±s.d., n=5) to −21.6±3.8 mV (CatCh, mean±s.d., n=5; FIG. 2e). In order to further quantify the increased Ca$^{++}$-permeability of CatCh, we performed Fura-2 calcium imaging on CatCh-expressing HEK293 cells and compared the measured 340/380 ratios to the ratios measured in WT ChR2-expressing cells.

Fura-2-Imaging on HEK293 Cells.

Fura-2 AM (5 mM; Invitrogen) was loaded at room temperature for 30 min to 1 hour. After loading the cells were recovered in a 140 mM NaCl solution without Ca$^{++}$ (140 mM NaCl, 7 mM EGTA, 2 mM MgCl$_2$ and 10 mM HEPES). Yellow fluorescent protein was excited by a 500 ms exposure to light using a 460/40 nm filter (Visitron Systems, Puchheim, Germany) to estimate each cell's expression level from its YFP-fluorescence. The solution was then replaced by an extracellular Ca$^{++}$-solution that consisted of 90 mM CaCl$_2$, 7 mM EGTA, 2 mM MgCl$_2$ and 10 mM HEPES. After 15 min in the dark the light-gated channels were stimulated for 10 s with blue light (460/40 nm). Fura-2 was excited with 340 nm (340/20) and 380 nm (380/20) and the emitted light (540/80 nm) detected with a CCD camera (all filters from Visitron Systems, Puchheim, Germany).

To exclude varying protein expression levels as a factor in calcium uptake, the measured 340/380 ratios were normalized to the YFP-fluorescence value of each individual cell. FIG. 2f shows that upon a 10-s blue-light (470 nm) photostimulation in saturating 90 mM Ca$^{++}$ solution, the intracellular Ca$^{++}$ increase in CatCh-expressing cells is about 4-times larger than in WT-expressing cells.

Application to Hippocampal Neurons

To test CatCh's suitability for neuronal application, the construct was expressed in cultured hippocampal pyramidal cells.

Hippocampal Neuron Culture.

Hippocampi were isolated from postnatal P1 Sprague-Dawley rats (Jackson Laboratory) and treated with papain (20 U ml$^{-1}$) for 20 min at 37° C. The hippocampi were washed with DMEM (Invitrogen/Gibco, high glucose) supplemented with 10% fetal bovine serum and triturated in a small volume of this solution. ~75,000 cells were plated on poly-D-lysine/laminin coated glass cover slips in 24-well plates. After 3 hours the plating medium was replaced by culture medium (Neurobasal A containing 2% B-27 supplement, 2 mM Glutamax-1 and 100 U/ml penicillin and 100 µg/ml streptomycin). ChR2(L132C)-YFP and ChR2-YFP were transfected 5-10 days after plating using the lipofectamine 2000 reagent (Invitrogen). Alternatively, 2-5×10$^9$ GC/ml of virus (AAV2/7-CAG-ChR2(L132C)-2A-EGFP-WPRE-bGH) was added to each well 4-9 days after plating. Expression became visible 5 days post-transduction. No neurotoxicity was observed for the lifetime of the culture (~5 weeks). No all-trans retinal was added to the culture medium or recording medium for any of the experiments described here.

Adeno-Associated Viral Vector Construction.

The cytomegalovirus early enhancer/chicken β-actin (CAG) promoter was PCR-amplified and inserted into pAAV2-Rho-EGFP (kind gift from Alberto Auricchio[28]) to obtain pAAV2-CAG-EGFP. The pAAV2-CAG-EGFP viral expression plasmid contained additionally a woodchuck posttranscriptional regulatory element (WPRE) and a bovine growth hormone (BGH) polyadenylation sequence. ChR2 (L132C)-2A-EGFP (kind gift from Volker Busskampö—2A self-cleaving peptide/CHYSEL[29]) was constructed by adapter PCR and subcloned into pAAV2-CAG-EGFP by replacement of EGFP using Clontech's in fusion kit. The viral vector (pAAV2-CAG-ChR2(L132C)-2A-EGFP-WPRE-bGH) was packaged (serotype 7) and affinity purified at the Gene Therapy Program of the University of Pennsylvania with a final infectious virus titer of 2.26×10$^{11}$ genome copies/ml.

Electrophysiological Recordings from Hippocampal Neurons.

For whole-cell recordings in cultured hippocampal neurons, patch pipettes with resistances of 5-10 MΩ were filled with 129 mM potassium gluconate, 10 mM HEPES, 10 mM KCl, 4 mM MgATP and 0.3 mM Na$_3$GTP, titrated to pH 7.2. Tyrode's solution was employed as the extracellular solution (125 mM NaCl, 2 mM KCl, 2 mM CaCl$_2$, 1 mM MgCl$_2$, 30 mM glucose and 25 mM HEPES, titrated to pH 7.4). The nominally Ca$^{++}$-free extracellular solution contained this same solution except that it had 0 mM Ca$^{++}$ and 3 mM Mg$^{++}$. Recordings were conducted in the presence of the excitatory synaptic transmission blockers, 1,2,3,4-tetrahydro-6-nitro-2,3-dioxo-benzo[f]quinoxaline-7-sulfonamide (NBQX, 10 μM, Sigma) and D(−)-2-Amino-5-phosphonopentanoic acid (AP-5, 50 μM, Sigma). For voltage-clamp recordings 1 μM tetrodotoxin was added to the extracellular solution. To inhibit BK-channel activity, 1 mM TEA was added. Recordings were conducted on an inverted Zeiss Axiovert 25 microscope equipped with a fluorescence lamp. Successful protein expression was proved by EGFP- or YFP-mediated fluorescence. Neuronal access resistance was 15-40 MΩ and was monitored for stability throughout the experiment. Electrophysiological signals were amplified using an Axopatch 200A amplifier (Axon Instruments, Union City, Calif.), filtered at 10 kHz, digitized with an Axon Digidata 1600 (50 Hz) and acquired and analyzed using pClamp9 software (Axon Instruments). Photocurrents were evoked using light pulses of various lengths from diode-pumped solid-state lasers (Pusch Opto Tech GmbH; $\lambda_1$=473 nm, $P_1$=100 mW, $\lambda_2$=532 nm, $P_2$=50 mW) or 10 ns flashes from an excimer pumped dye laser (Coumarin 2, $\lambda$=450 nm). Specific light intensities are indicated in the figure legends and the text and are intensities at the end of a 400 μm diameter quartz optic fiber (STE-F100/400-Y-VIS/NIR; Laser 2000, Wessling, Germany) at a distance of ~500 μm from the cell. Currents measured from neurons expressing ChR2(L132C)-YFP and ChR2(L132C)-2A-EGFP were identical.

Confocal Imaging.

For imaging, cover-slips with hippocampal neurons were fixed at 4° C. for 10 min in 4% paraformaldehyde in PBS buffer containing 2% sucrose. The cells were subsequently incubated for 1.5 hours in rabbit α-GFP IgG (Invitrogen, A11122) followed by a 45 min incubation in Alexa Fluor 488 donkey-α-rabbit IgG (Invitrogen, A21206). Immunofluorescence of mounted cover-slips was photographed on a Zeiss LSM 510 confocal microscope (Zeiss, Plan-Neofluar 40×/0.75).

Figure 3:
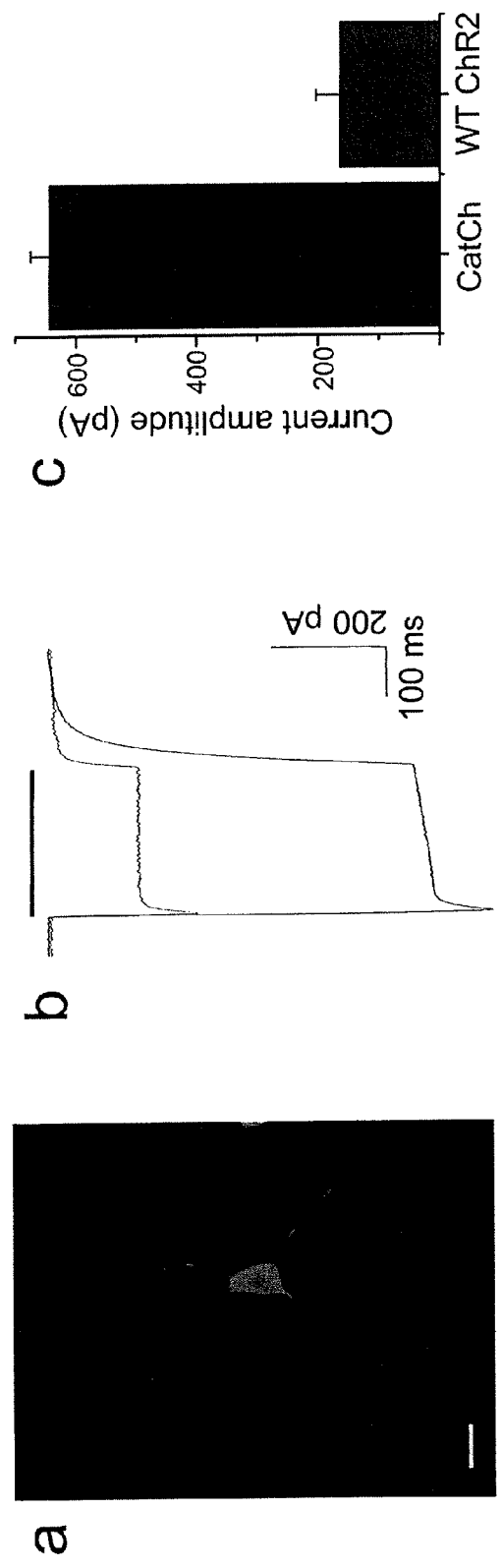
FIG. 3 CatCh-expression in hippocampal cultured neurons. (a) Confocal image of a cultured hippocampal neuron expressing ChR2(L132C)-2A-EGFP under the CAG promoter. Scale bar 20 μm. (b) Comparison of typical photocurrents of CatCh (black) and WT (red) evoked by a 600 ms pulse of 473-nm blue light ($J_{473nm}$ 1×10$^{19}$ photons s$^{-1}$ cm$^{-2}$). (c) Summary of steady-state current amplitudes (−60 mV, n=6).
Figure 4:
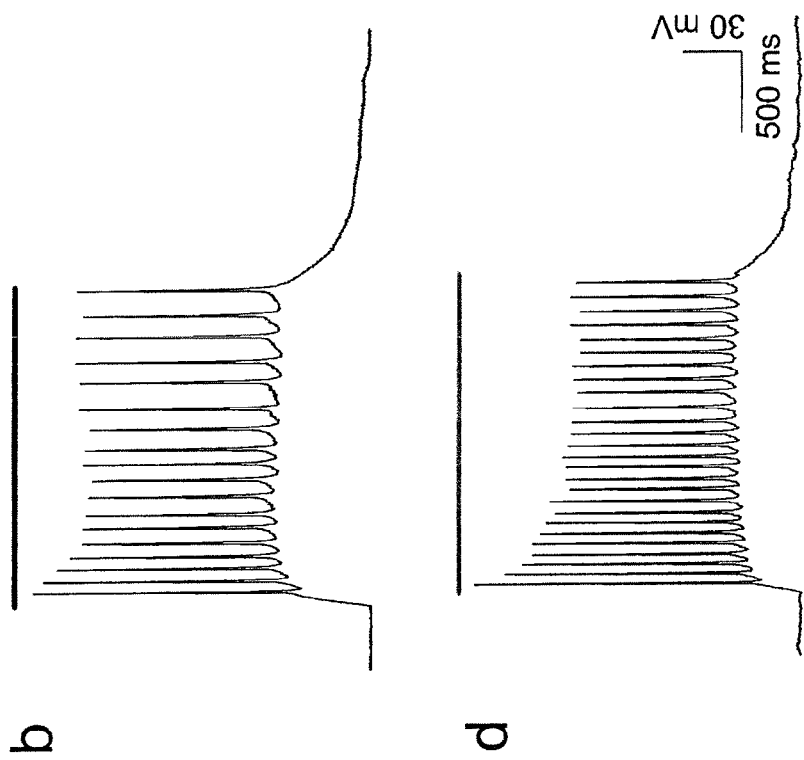
FIG. 4 Fast and high-sensitivity neural photostimulation. (a-d) Representative whole cell current-clamp recordings from a CatCh-expressing hippocampal neuron in response to 2-s light pulses. (a) The 473-nm light intensity required for the WT induces a depolarization block ($J_{473nm}$ 2.5×10$^{17}$ photons s$^{-1}$ cm$^{-2}$). (b) Reducing the light intensity re-establishes firing ($J_{473nm}$ 2.5×10$^{16}$ photons s$^{-1}$ cm$^{-2}$). (c) Representative light-tuning curve for spike-firing ($J_{max}$ 9.7×10$^{16}$ photons s$^{-1}$ cm$^{-2}$, mean±s.d., 2 runs). (d) Moderate green 532-nm illumination also evokes trains of action potentials ($J_{532nm}$ 2.5×10$^{17}$ photons s$^{-1}$ cm$^{2}$). (e) Light pulse-to-spike peak latency throughout light pulse trains consisting of 25 1-ms 473-nm light pulses ($J_{473nm}$ 3×10$^{18}$ photons s$^{-1}$ cm$^{2}$, mean±s.d. [jitter]), in 2 mM extracellular $Ca^{++}$ (■) and as control at 5 Hz in 3 mM extracellular $Mg^{++}$ (■), which increases latency to values similar of WT ChR2. (f) Spike firing in response to 1-ms 473-nm pulses at a rate of 50 Hz ($J_{473nm}$ 2.8×10$^{19}$ photons s$^{-1}$ cm$^{-2}$) and (g) in response to 10 ns 473-nm light pulses at 10 Hz ($J_{473nm}$ 1.1×10$^{25}$ photons s$^{-1}$ cm$^{2}$). (h) Incomplete membrane repolarization (double-headed arrow) due to inhibition of BK channels by 1 mM TEA. Overlay of 3rd spike of pulse train (black), 1$^{st}$ spike (red) and 3$^{rd}$ spike (blue) after TEA application ($J_{473nm}$ 1.8×10$^{18}$ photons s$^{-1}$ cm$^{-2}$). (i) Replacement of $Ca^{++}$ by $Mg^{++}$ in the extracellular solution slows spike repolarization and causes prolonged depolarization (5 Hz, left) and the formation of multiple spikes at higher frequencies (20 Hz, right) ($J_{473nm}$ 8.3×10$^{18}$ photons s$^{-1}$ cm$^{-2}$).
Figure 4:
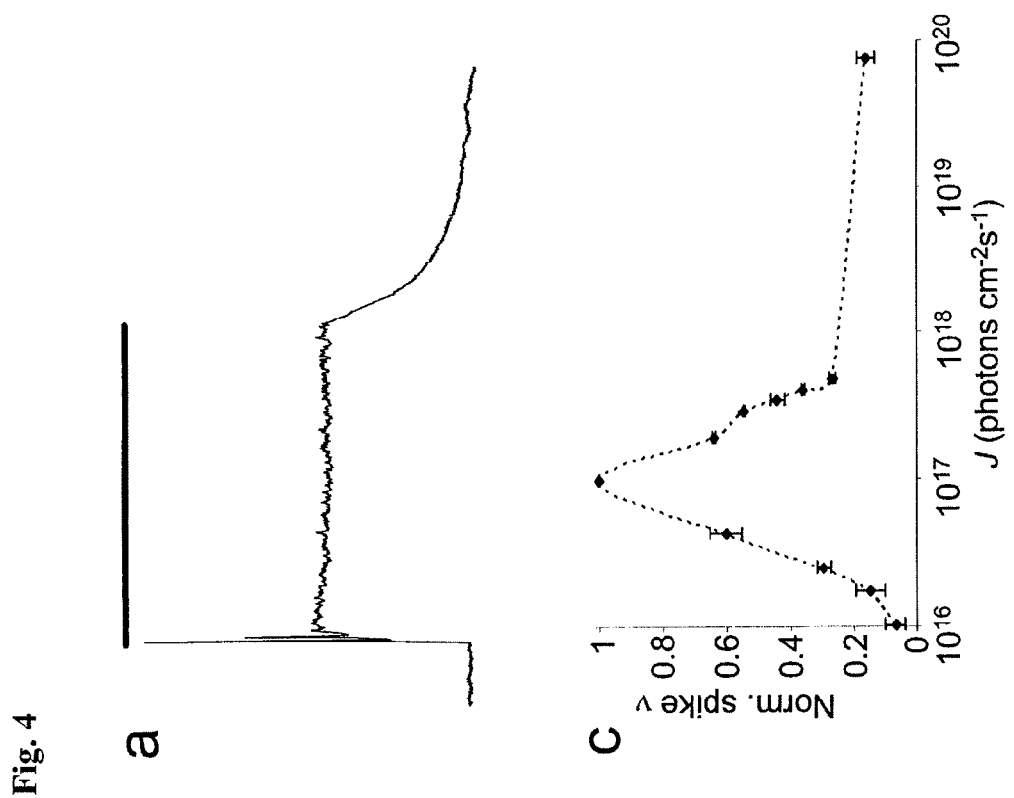
Figure 4:
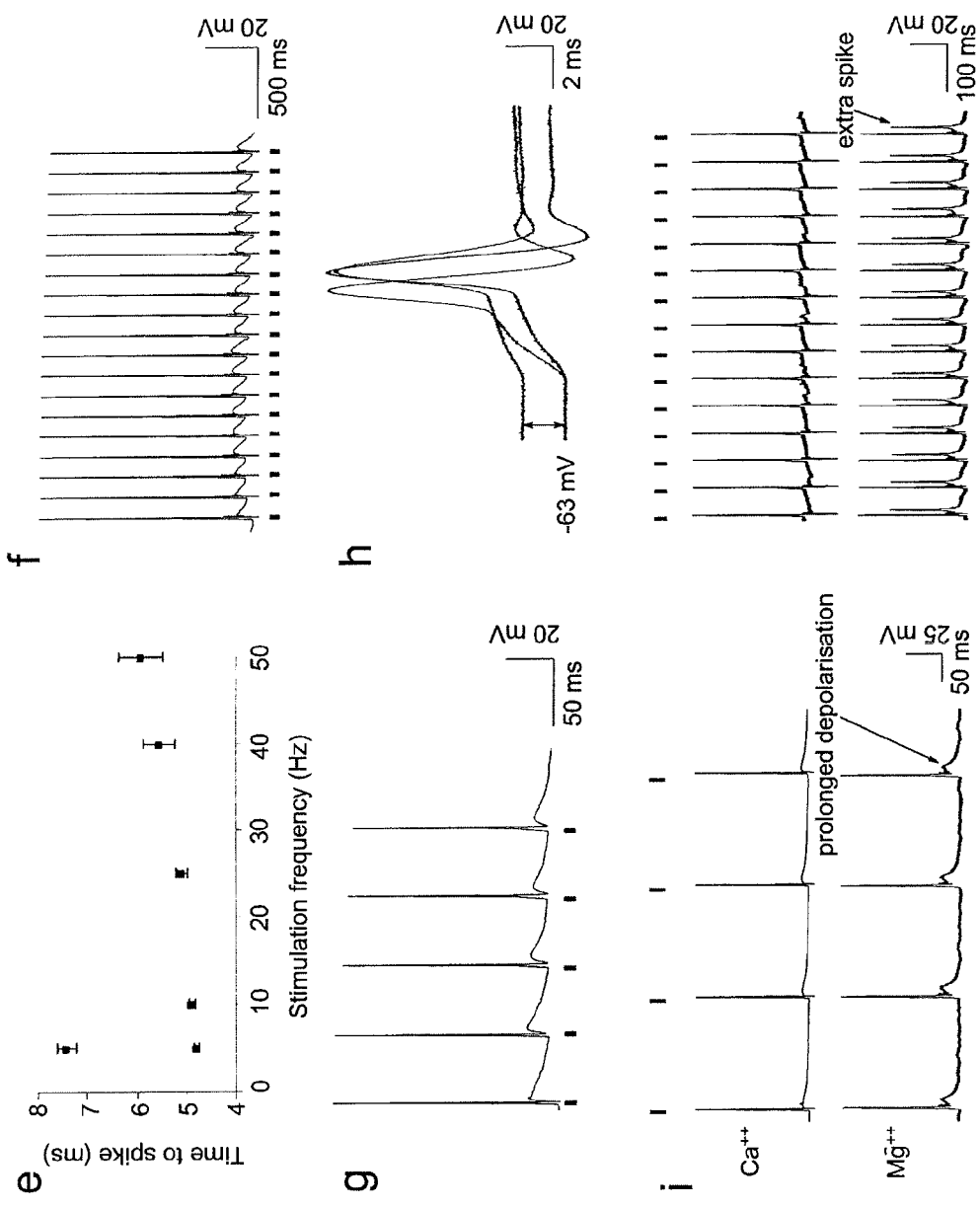
Figure 7:
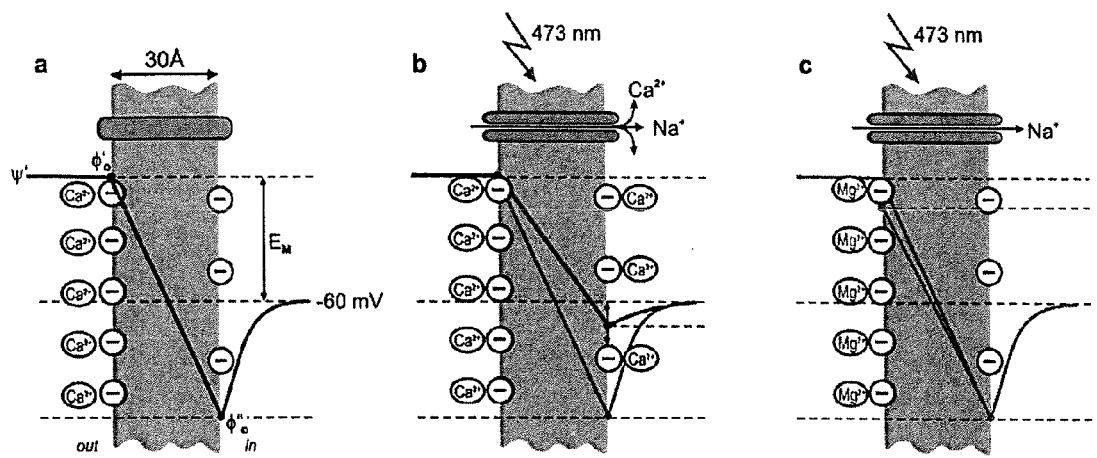
FIG. 7 Surface potential changes induced by $Ca^{++}$. It is known, that the voltage drop across the membrane depends on the applied potential difference (Ψ') and is modified by the surface potential ($\Phi_0$). In general $\Phi_0$ depends on the negative surface charge density, which can be modified by screening with counterions. Therefore the activation of the voltage-gated sodium channels (and other voltage-sensitive channels) can be influenced by the change of the surface charge either on the external or internal side of the membrane[18]. In our case, the $Ca^{++}$ conducted through CatCh neutralizes the negative surface charges on the inner membrane face of the neuron. By this a depolarizing effect on the membrane potential is induced, leading to the induction of action potentials at lower light intensities. A schematic drawing of this mechanism is depicted in a-c (after Hille 2001). (a) In the dark, the CatCh channel is closed, the potential difference over the membrane, $E_M$ (applied external potential), is equivalent to the resting membrane potential (here set to −60 mV). For simplicity, $\Phi_0$ was set to $\Phi_0$'. (b) Upon light-activation of CatCh, the usual membrane depolarizing $Na^+$ influx occurs. However, the additional $Ca^{++}$ that enters the neuron increases the surface potential on the inner membrane face ($\Phi_0$"). The higher the $Ca^{++}$ influx, the more positive $\Phi_0$" (indicated by double-headed arrow) and the smaller the voltage-drop across the membrane. This facilitates activation of voltage-gated sodium channels. (c) By replacing extracellular $Ca^{++}$ with $Mg^{++}$, which does not permeate through CatCh and is already present to ~4 mM in the cytosol, only a minor depolarizing effect occurs. This is due to a weaker binding of $Mg^{++}$ to the extracellular membrane side compared to $Ca^{++}$, which slightly lowers the extracellular surface potential $\Phi_0$'. Notice that the depolarizing effect of the surface potential increases with decreasing the slope of the voltage-drop across the membrane.

The CatCh mutant was robustly expressed in hippocampal cultures (FIG. 3a) for weeks without signs of neurotoxicity and exhibited, as in HEK293 cells, a higher steady state-to-peak ratio in whole-cell recordings and about four-fold increased current amplitudes of 644±31 pA (−60 mV, n=6, mean±s.d.) compared to the WT with 164±39 pA (−60 mV, n=6, mean±s.d.) in response to 473-nm blue light (FIG. 3b). In current clamp mode, artificially high light intensities typically used to activate the WT ($10^{18}$-$10^{19}$ photons $s^{-1}$ $cm^{-2}$) drove CatCh-expressing pyramidal cells into a depolarization block (FIG. 4a). To induce reliable spike trains, the light intensity was reduced by 2 log units ($5*10^{16}$-$2*10^{17}$ photons $s^{-1}$ $cm^{-2}$) to a light intensity within the natural range of cone photoreceptor driven photopic vision (FIG. 4b)[17]. FIG. 4c shows a representative tuning curve for the light-intensity dependent firing rate of a pyramidal cell. The averaged maximum firing rate lies at $8.2\times10^{16}\pm2.5\times10^{16}$ photons $s^{-1}$ $cm^{-2}$ (mean±s.d., n=5). The higher light efficacy of CatCh-expressing neurons facilitates activation with wavelengths away from the peak sensitivity, as exemplified for green light (532 nm) in FIG. 4d. This may confer benefits in terms of more effective tissue recruitment with deeper-penetrating green light. We assign the dramatically enhanced light sensitivity of CatCh-expressing neurons to an increased $Ca^{++}$ permeability, thereby transiently increasing the surface potential on the cytosolic membrane surface[10,11,18,19] (for an explanation of the $Ca^{++}$ effect on the surface potential see FIG. 7). During light excitation, CatCh serves as a membrane bound fast $Ca^{++}$-source, by temporarily increasing the local intracellular surface $Ca^{++}$ concentration, thereby neutralizing the negative surface charges (FIG. 7). It is known that this causes a shift of the internal surface potential to more positive values thus depolarizing the membrane (FIG. 7)[11,18]. A consequence is that voltage-gated $Na^+$-channels are activated at more negative membrane potentials[18]. After short light pulses or after switching off the stationary light, $Ca^{++}$ equilibrates rapidly (microseconds) within the cytoplasm, leading to a rapid recovery and the immediate disappearance of action potentials. Thus, for CatCh, less photocurrent and subsequently less light is required for spike initiation compared to WT ChR2. The light pulse-to-spike latency in CatCh was faster (~5-6 ms; FIG. 4e) with a smaller jitter than the latency for WT ChR2 (~10 ms) at similar light intensities ($2.8\times10^{18}$ photons $s^{-1}$ $cm^{-2}$)[3]. The inventors further tested CatCh for its ability to induce single action potentials at high frequency light-stimulation. A train of 1-ms long blue 473-nm light pulses ($2.8\times10^{19}$ photons $s^{-1}$ $cm^{-2}$) drove 100% reliable spike trains up to frequencies of 50 Hz (n=8, FIG. 4f—most pyramidal cells do not follow well beyond 50 Hz even with direct current injection). The WT, on the other hand, requires at least 2-ms light pulses to induce spikes reliably and does this only up to frequencies of 20 Hz[12]. We pushed the short activation times of CatCh even further and evoked single action potentials up to frequencies of 10 Hz by 10 ns blue light pulses ($1.1\times10^{25}$ photons $s^{-1}$ $cm^{-2}$), a pulse length short enough to only induce a single turnover in each CatCh protein (FIG. 4g). However, fast stimulation frequencies also require a fast repolarization of the cell after each spike. Despite a decelerated $\tau_{off}$ of CatCh compared to the WT, the ~4-fold increase in $Ca^{++}$-influx during CatCh activation (see Fura-2 measurements FIG. 2f) appears to suffice to activate enough $Ca^{++}$-activated large conductance potassium channels (BK channels)[20] to potently repolarize the cell to its original resting potential within milliseconds after each action potential. To prove that the fast repolarization was mediated through BK channels, we added 100 μM of the potassium channel inhibitor tetraethylammonium (TEA) to the extracellular solution and observed incomplete membrane repolarization and the generation of a plateau potential typically seen in pulse stimulation protocols with the WT ChR2[3] (FIG. 4h).

Taken together, CatCh-expressing neurons exhibit a faster spike onset, a faster repolarization and an increased light-sensitivity compared to WT-expressing cells (for a comparison see table 1). Control experiments in the absence of external $Ca^{++}$ and in the presence of 3 mM $Mg^{++}$, which has a less pronounced effect on the surface potential[11,18] (FIG. 7) and is not conducted through WT ChR2 or CatCh, support the above interpretations: 1) The light pulse-to-spike latency increased to WT ChR2 values (FIG. 4e), 2) Instead of the fast spike repolarization as observed in the presence of $Ca^{++}$, a prolonged artificial depolarization similar to what is seen in WT ChR2 experiments was observed (FIG. 4i, left), 3) In the absence of $Ca^{++}$, identical light intensities resulted in a reduced depolarization by ~10 mV under otherwise equal experimental conditions and 4) Multi-spiking as expected from the prolonged open time of CatCh reoccurs in the absence of $Ca^{++}$ (FIG. 4i, right).

Thus, the inventors have demonstrated that CatCh, a channelrhodopsin with an elevated $Ca^{++}$-permeability, pairs increased light-sensitivity with fast kinetics and thus outperforms the WT ChR2 and the published slow and fast mutants (for a comparison of the properties of different ChR2 variants see table 1).

Discussion

At first glance CatCh, the L132C mutant of WT ChR2, shows rather unspectacular results in comparison to the WT ChR2: 1) a two-fold increase of the life-time of the open state, 2) a decelerated decay of the P520 intermediate in the photocycle kinetics, 3) an unchanged single channel conductance, and 4) a marginally red-shifted absorption maximum (4 nm). A 2.5-fold increased photocurrent can be easily explained by the measured parameters with no relevant increase in expression level. At second glance, however, closer inspection of the voltage-clamp data obtained from CatCh expressing *Xenopus laevis* oocytes gave a first indication towards an elevated $Ca^{++}$-permeability, which was then confirmed by the determination of the reversal potential and calcium imaging experiments on HEK293 cells. Looking at the model in FIG. 1, an increase in $Ca^{++}$-permeability might be facilitated by the formation of a more flexible structure and thus the formation of a cavity, as shown for the L94A mutation of the light-driven proton pump bacteriorhodopsin (compare FIG. 1)[21]. This cavity would be located in a hydrophobic patch as part of the conserved transmembrane helix three (TM3), only a helical turn apart from C128. Manipulating the interaction between C128 (TM3) and D156 (TM4) decelerates the reaction cycle of ChR2 dramatically[5,6], an effect that was also observed in the bacteriorhodopsin mutant L93A[22, 23], i.e. the neighboring residue of L94. In ChR2, the interaction of TM3 and TM4 seems to affect both gating and selectivity, pointing to a structural element as transducer of the light reaction to the ion pore[24]. Insertion of the smaller and more hydrophilic cysteine could increase the flexibility of the helical segment, facilitating the access of $Ca^{++}$.

When delivered to hippocampal pyramidal cells, CatCh exhibited a ~70-fold increase in light-sensitivity compared to WT ChR2. Usually, such an increased light efficacy is accompanied by a strongly prolonged open channel life-time[2,6,13]. This is not the case for CatCh. The observed light sensitivity differs markedly from what has been observed for other channelrhodopsins up to now. As explained below, the secondary effects on neuronal excitability are induced by $Ca^{++}$ influx through CatCh. Despite having a slower closing kinetics compared to the WT, CatCh shows increased spike-reliability and precision during high-frequency light-stimulation, reducing extra spikes and eliminating artificial plateau potentials typically observed in WT-expressing cells at stimulation frequencies above 20 Hz[3,7,12]. 1-ms light pulses delivered at room temperature induced reliable spike trains up to 50 Hz in CatCh-expressing pyramidal cells (their natural limit of natural spiking; FIG. 4*f*). Higher frequency CatCh-mediated spike induction on faster spiking cells such as cortical paravalbumin interneurons remains to be tested[12]. Since channelrhodopsin kinetics are temperature dependent with a $Q_{10}$ of ~2.3[14], the inventors would expect a 3.2-fold accelerated CatCh kinetics for in vivo experiments at 37° C. without loosing light sensitivity. This would allow CatCh-mediated spike stimulation up to at least 300 Hz. The increased light-sensitivity combined with the fast kinetics and high temporal precision allowed us to activate CatCh with light-pulses as short as 10 ns, which activate a single turnover in each CatCh molecule followed by a single spike. The observations in excitable cells are best explained by the increased $Ca^{++}$ influx into the neuron during illumination. Note that the $Ca^{++}$ contribution to the driving force due to its increased permeability can be neglected. However, we can consider CatCh as a light-gated membrane bound $Ca^{++}$ source ("a membrane bound caged $Ca^{++}$"), which transiently delivers $Ca^{++}$ to the cytosolic surface of the cell membrane as long as the CatCh channel is open. This temporarily neutralizes the negative charges on the inner membrane face, thereby increasing the surface potential, which is equivalent to a depolarization of the membrane[11] (FIG. 7). As expected, when extracellular $Ca^{++}$ was replaced by the non-permeating $Mg^{++}$, all the observed $Ca^{++}$ effects on the action potential were abolished, restoring the phenotype of WT ChR2. This proves that the observed $Ca^{++}$ effects were due to influx of extracellular $Ca^{++}$ and not caused by a rise of $[Ca^{++}]_i$ through a potential expression of CatCh in the cell organelles like the endoplasmatic reticulum. The fast initial depolarization via the surface potential halves the light pulse-to-peak latency from ~10 ms in WT ChR2 expressing cells[3] to ~5 ins in CatCh expressing cells. Compared to the WT ChR2, the peak-stationary current ratio is much reduced in CatCh (see table 1). Therefore, during sustained illumination of CatCh, the cell's depolarization level remains almost stationary. The continuous $Ca^{++}$-influx during persistent illumination may activate calcium-activated non-selective cation channels, which further support the maintenance of a stationary depolarization level. On the other hand, a prerequisite for successful high-frequency pulsed stimulation is a fast repolarization of the cell following each action potential. The slightly increased lifetime of the open state of CatCh compared to the WT should limit its maximal stimulation frequency. However, an enhanced $Ca^{++}$-permeability counteracts this limitation by potent activation of large conductance calcium-gated potassium channels (BK channels). This re-establishes the resting membrane potential of the neuron within milliseconds after each action potential. This theory was confirmed by the inhibition of BK channels with the open-channel blocker TEA, which resulted in a persistent depolarization of the neuron during the length of a pulse stimulation protocol.

In comparison to already available optogenetic tools, CatCh has an increased light-sensitivity similar to the slow-mutants[13] or SFO's[6] but with much accelerated response kinetics owing to its increased $Ca^{++}$-permeability and the consequences on neuronal excitability. This makes CatCh superior to available ChR2 variants, where a high light sensitivity had to be established at cost of fast kinetics and vice versa with respect to the fast channelrhodopsins[7,12] (for an overview see table 1).

With regard to optogenetic application, we note that it will be important to validate the optimal light-pulse parameters in each experimental preparation such as stimulation length and intensity, as the specific response will ultimately be controlled by intrinsic biophysical properties of the neuron and CatCh expression levels.

TABLE 1

Comparison of properties of CaTCh with other excitatory optogenetic tools

| | $\tau_{on}$ [ms] | $\tau_{off}$ [ms, s] | $\gamma$ [fS] | I (pA) stat | $I_{stat}/I_{max}$ | $\lambda_{max}$ (nm) | J (ph s$^{-1}$ cm$^{-2}$) [EC50 (mW/mm$^2$)] | max spike v | $p_{Ca}/p_{Na}$ | AD | Ref |
|---|---|---|---|---|---|---|---|---|---|---|---|
| CaTCh | 0.6 ± 0.003 | 15 ± 2 ms | 140 ± 5 | 643.8 ± 30.9 | 0.71 ± 0.16 | 474 | $10^{16}$-$10^{17}$ 70x lower WT [0.7] | ≥50 Hz | 0.24 | No | |
| WT ChR2 | 0.2 ± 0.002 | 10 ± 1 ms | ~150[b] | 216.3 ± 39.0 | 0.37 ± 0.18 | 470 | $5 \times 10^{17}$-$10^{19}$ [0.7] | ≤20 Hz | 0.15 | Yes | [2, 3, 14] |

TABLE 1-continued

Comparison of properties of CaTCh with other excitatory optogenetic tools

| | | $\tau_{on}$ [ms] | $\tau_{off}$ [ms, s] | $\gamma$ [fS] | I (pA) stat | $I_{stat}/I_{max}$ | $\lambda_{max}$ (nm) | J (ph s$^{-1}$ cm$^{-2}$) [EC50 (mW/mm$^2$)] | max spike ν | $p_{Ca}/p_{Na}$ | AD | Ref |
|---|---|---|---|---|---|---|---|---|---|---|---|---|
| ChR2 H134R | | ~0.6 | 19 ± 2 ms | ~150[b] | ~1.5 × $I_{WT}$ | 0.53 ± 0.09 | 450 | 5 × 10$^{17}$-10$^{19}$ [0.7] | ~20 Hz | — | Yes | [1, 7, 14] |
| SFO's, slow mutants | C128T | 9 ± 1.6 | 2 ± 0.5 s | — | ~0.73 × $I_{WT}$ | ~0.5 | 480 | 5 × 10$^{17}$-10$^{19}$ [0.03] | c | — | Yes | [5, 6] |
| | C128A | 5.7 ± 1.0 | 52 ± 2 s | — | ~0.30 × $I_{WT}$ | ~0.7 | 480 | 5 × 10$^{17}$-10$^{19}$ [0.01] | c | — | Yes | |
| | C128S | 30 ± 7.5 | 106 ± 9 s | — | ~0.25 × $I_{WT}$ | ~0.85 | 480 | 5 × 10$^{17}$-10$^{19}$ [0.01] | c | — | Yes | |
| | D156A | 3.3 ± 0.1 | >150 s[a] | — | ~$I_{WT}$ | ~1 | 480 | 5 × 10$^{17}$-10$^{19}$ [0.01] | d | — | Yes | |
| ChETA | | — | 4.8 ± 0.6 ms | — | ~0.9 × $I_{WT}$ | 0.6 ± 0.04 | 500 | 10$^{18}$-10$^{19}$ less sensitive than WT | 200 Hz | — | No | [12] |
| ChIEF | | — | 9.8 ± 0.7 ms | — | ~3 × $I_{WT}$ | ~0.8 | 450 | 10$^{18}$-10$^{19}$ less sensitive than WT [0.92] | 25 Hz | 0.12 | Yes | [7] |

$\tau_{on}$: values from single turnover measurements, γ: in 200 mM guanidine-HCl, RT, −60 mV I: HCN, −60 mV; $I_{WT}$ = WT ChR2 current under respective experimental conditions, J: light intensity required to induce action potential; EC50: apparent half-saturating light intensities, max spike ν: maximal light-pulse induced reliable spike frequency, AD: artificial after depolarization,

[a] data cannot be determined accurately and represents lower limit estimation,

[b] extrapolated value, c subthreshold depolarization, d two-color on/off control with blue-yellow

LIST OF REFERENCES

WO 03/084994

1. Nagel, G. et al. Channelrhodopsin-2, a directly light-gated cation-selective membrane channel. *Proc Natl Acad Sci USA* 100, 13940-13945 (2003).
2. Nagel, G. et al. Light activation of channelrhodopsin-2 in excitable cells of *Caenorhabditis elegans* triggers rapid behavioral responses. *Curr Biol* 15, 2279-2284 (2005).
3. Boyden, E., Zhang, F., Bamberg, E., Nagel, G. & Deisseroth, K. Millisecond-timescale, genetically targeted optical control of neural activity. *Nat Neurosci* 8, 1263-1268 (2005).
4. Zhang, F. et al. Multimodal fast optical interrogation of neural circuitry. *Nature* 446, 633-639 (2007).
5. Bamann, C., Gueta, R., Kleinlogel, S., Nagel, G. & Bamberg, E. Structural guidance of the photocycle of channelrhodopsin-2 by an interhelical hydrogen bond. *Biochemistry* 49, 267-278 (2010).
6. Berndt, A., Yizhar, O., Gunaydin, L., Hegemann, P. & Deisseroth, K. Bi-stable neural state switches. *Nat Neurosci* 12, 229-234 (2009).
7. Lin, J., Lin, M., Steinbach, P. & Tsien, R. Characterization of engineered channelrhodopsin variants with improved properties and kinetics. *Biophys J* 96, 1803-1814 (2009).
8. Lagali, P. et al. Light-activated channels targeted to ON bipolar cells restore visual function in retinal degeneration. *Nat Neurosci* 11, 667-675 (2008).
9. Bi, A. et al. Ectopic expression of a microbial-type rhodopsin restores visual responses in mice with photoreceptor degeneration. *Neuron* 50, 23-33 (2006).
10. Frankenhäuser, B. & Hodgkin, A. The action of calcium on the electrical properties of squid axons. *J Physiol (Lond)* 137, 218-244 (1957).
11. Hille, B. 649-662 (Sinauer Associates, Sunderland Mass. USA, 2001).
12. Gunaydin, L. et al. Ultrafast optogenetic control. *Nat Neurosci* 13, 387-392 (2010).
13. Bamann, C., Kirsch, T., Nagel, G. & Bamberg, E. Spectral characteristics of the photocycle of channelrhodopsin-2 and its implication for channel function. *J Mol Biol* 375, 686-694 (2008).
14. Feldbauer, K. et al. Channelrhodopsin-2 is a leaky proton pump. *Proc Natl Acad Sci USA* (2009).
15. Caldwell, J. et al. Increases in intracellular calcium triggered by channelrhodopsin-2 potentiate the response of metabotropic glutamate receptor mGluR7. *J Biol Chemistry* 283, 2430024307 (2008).
16. Weber, W.-M. Ion currents in *Xenopus laevis* oocytes: state of the art. *Biochim Biophys Acta* 1421, 213-233 (1999).
17. Thyagarajan, S. et al. Visual function in mice with photoreceptor degeneration and transgenic expression of channelrhodopsin 2 in ganglion cells. *J Neurosci* 30, 8745-8758 (2010).
18. Hille, B., Woodhull, B. & Shapiro, B. Negative surface charge near sodium channels of nerve: divalent ions, monovalent ions, and pH. *Philos Trans R Soc Lond B Biol Sci* 270, 301-318 (1975).
19. Muller, R. & Finkelstein, A. The effect of surface charge on the voltage-dependent conductance induced in thin lipid membranes by monazomycin. *J General Physiol* 60, 285-306 (1972).
20. Faber, E. & Sah, P. Calcium-activated potassium-channels: multiple contributions to neuronal function. *Neuroscientist* 9, 181-194 (2003).
21. Joh, N., Oberai, A., Yang, D., Whitelegge, J. & Bowie, J. Similar energetic contributions of packing in the core of membrane and water-soluble proteins. *J Am Chem Soc* 131, 10846-10847 (2009).

22. Subramaniam, S., Faruqi, A., Oesterhelt, D. & Henderson, R. Electron diffraction studies of light-induced conformational changes in the Leu-93→Ala bacteriorhodopsin mutant. *Proc Nat Acad Sci USA* 94 1767-1772 (1997).
23. Subramaniam, S., Greenhalgh, D., Rath, P., Rothschild, K. & Khorana, H. Replacement of leucine-93 by alanine or threonine slows down the decay of the N and O intermediates in the photocycle of bacteriorhodopsin: implications for proton uptake and 13-cis-retinal all-trans-retinal reisomerization. *Proc Natl Acad Sci USA* 88, 6873-6877 (1991).
24. Nack, M. et al. The DC gate in Channelrhodopsin-2: crucial hydrogen bonding interaction between C128 and D156. *Photochemical & Photobiological Sciences* 9, 194-198 (2010).
25. Busskamp, V. et al. Genetic reactivation of cone photoreceptors restores visual responses in retinitis pigmentosa. *Science* 329, 413-417 (2010).
26. Ellis-Davies, G. C. R. Neurobiology with caged calcium. *Chem Rev* 108, 1603-1613 (2008).
27. Lorenz, C., Pusch, M. & Jentsch, T. Heteromultimeric ClC chloride channels with novel properties. *Proc Natl Acad Sci USA* 92, 13362-13366 (1996).
28. Allocca, M. et al. Novel adeno-associated virus serotypes efficiently transduce murine photoreceptors. *J Virology* 81, 11372-11380 (2007).
29. de Felipe, P. et al. E unum pluribus: multiple proteins from a self-processing polyprotein. *Trends Biotechnol* 24, 68-75 (2006).
30. Humphrey, W., Dalke, A. and Schulten, K. VMD—Visual Molecular Dynamics. *J Molec Graphics* 14, 33-38 (1996).

---

The invention claimed is:

1. A light-inducible ion channel, comprising the amino acid sequence shown in positions 1-309 of SEQ ID NO: 1, and a substitution at a position corresponding to L132 in SEQ ID NO: 1 selected from the group consisting of L132C, L132S, L132E, L132D, and L132T.

2. The light-inducible ion channel of claim 1, wherein
   (a) a light-sensitivity is increased by more than 5 times, as compared to a wild-type CHOP-2 in a hippocampal neuron;
   (b) a calcium conductivity is increased by at least two-fold, as compared to a wild-type CHOP-2, as determined by Fura-2-imaging on HEK293 cells; or
   (c) a stimulation frequency is increased by at least 1.5-fold, as compared to the wild-type CHOP-2 as determined by whole-cell electrophysiological recordings in a hippocampal neuron.

3. The light-inducible ion channel of claim 1, further comprising at least one amino acid residue selected from the group consisting of: aspartic acid at a position corresponding to position 253 of SEQ ID NO: 1; lysine at a position corresponding to position 257 of SEQ ID NO: 1; tryptophan at a position corresponding to position 260 of SEQ ID NO: 1; glutamic acid at a position corresponding to position 123 of SEQ ID NO: 1; histidine or arginine at a position corresponding to position 134 of SEQ ID NO: 1; threonine, serine, or alanine at a position corresponding to position 128 of SEQ ID NO: 1; and alanine at a position corresponding to position 156 of SEQ ID NO: 1.

4. The light-inducible ion channel of claim 1, further comprising a consensus motif L(I)DxxxKxxW(F,Y).

5. A channelrhodopsin, comprising:
   the light-inducible ion channel of claim 1, and
   a retinal or a retinal derivative, wherein the retinal derivative is optionally selected from the group consisting of 3,4-dehydroretinal; 13-ethyiretinal; 9-dm-retinal; 3-hydroxyretinal; 4-hydroxyretinal; naphthylretinal; 3,7,11-trimethyl-dodeca-2,4,6,8,10-pentaenai; 3,7-dimethyl-deca-2,4,6,8-tetraenal; 3,7-dimethyl-octa-2,4,6-trienal; a 6-7 rotation-blocked retinal; a 8-9 rotation-blocked retinal; and a 10-11 rotation-blocked retinal.

6. A nucleic acid construct, comprising a nucleotide sequence coding for the light-inducible ion channel of claim 1.

7. An expression vector, comprising the nucleic acid construct of claim 6, wherein the expression vector is optionally suitable for gene therapy.

8. A cell comprising the channelrhodopsin of claim 5.

9. The cell of claim 8, wherein the cell is a mammalian cell, an insect cell, or a yeast cell.

10. The cell of claim 9, wherein the mammalian cell is
    (a) a photoreceptor cell, a retinal rod cell, a retinal cone cell, a retinal ganglion cell, a bipolar neuron, a ganglion cell, a pseudounipolar neuron, a multipolar neuron, a pyramidal neuron, a Purkinje cell, or a granule cell; or
    (b) a melanoma cell, a COS cell, a BHK cell, a HEK293 cell, a CHO cell, a myeloma cell, or a MDCK cell.

11. A pharmaceutical composition, comprising the light-inducible ion channel of claim 1.

* * * * *

UNITED STATES PATENT AND TRADEMARK OFFICE
CERTIFICATE OF CORRECTION

PATENT NO. : 8,748,578 B2
APPLICATION NO. : 13/821353
DATED : June 10, 2014
INVENTOR(S) : Ernst Bamberg et al.

Page 1 of 1

It is certified that error appears in the above-identified patent and that said Letters Patent is hereby corrected as shown below:

On the title page, Item (73), the Assignee's Information is incorrect. Item (73) should read:

--(73)  Assignee: Max—Planck-Gesellschaft zur Foerderung der Wissenschaften e.V., Munich (DE)--

Signed and Sealed this
Sixteenth Day of September, 2014

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 737
<212> TYPE: PRT
<213> ORGANISM: Chlamydomonas reinhardtii

<400> SEQUENCE: 1

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255
```

```
Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
                340                 345                 350

Arg Ala Ala Met Met Met Met Asn Gly Asn Gly Met Gly Met Gly Met
                355                 360                 365

Gly Met Asn Gly Met Asn Gly Met Gly Gly Met Asn Gly Met Ala Gly
            370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415

Gln Phe Ala Gln Leu Ser Val Thr Tyr Glu Leu Val Pro Ala Leu Gly
                420                 425                 430

Ala Asp Asn Thr Leu Ala Leu Val Thr Gln Ala Gln Asn Leu Gly Gly
                435                 440                 445

Val Asp Phe Val Leu Ile His Pro Glu Phe Leu Arg Asp Arg Ser Ser
                450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gln Gly Ile Leu
                500                 505                 510

Pro Ala His Ile Val Ala Leu Val Ala Lys Met Gln Gln Met Arg Lys
                515                 520                 525

Met Gln Gln Met Gln Gln Ile Gly Met Met Thr Gly Gly Met Asn Gly
                530                 535                 540

Met Gly Gly Gly Met Gly Gly Gly Met Asn Gly Met Gly Gly Gly Asn
545                 550                 555                 560

Gly Met Asn Asn Met Gly Asn Gly Met Gly Gly Gly Met Gly Asn Gly
                565                 570                 575

Met Gly Gly Asn Gly Met Asn Gly Met Gly Gly Asn Gly Met Asn
                580                 585                 590

Asn Met Gly Gly Asn Gly Met Ala Gly Asn Gly Met Gly Gly Gly Met
            595                 600                 605

Gly Gly Asn Gly Met Gly Gly Ser Met Asn Gly Met Ser Ser Gly Val
                610                 615                 620

Val Ala Asn Val Thr Pro Ser Ala Ala Gly Met Gly Gly Met Met
625                 630                 635                 640

Asn Gly Gly Met Ala Ala Pro Gln Ser Pro Gly Met Asn Gly Arg
                645                 650                 655

Leu Gly Thr Asn Pro Leu Phe Asn Ala Ala Pro Ser Pro Leu Ser Ser
                660                 665                 670
```

-continued

```
Gln Leu Gly Ala Glu Ala Gly Met Gly Ser Met Gly Gly Met Gly Gly
            675                 680                 685

Met Ser Gly Met Gly Gly Met Gly Gly Met Gly Gly Met Gly Gly Ala
        690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu
```